United States Patent
Melander et al.

(10) Patent No.: US 9,221,765 B2
(45) Date of Patent: Dec. 29, 2015

(54) INHIBITION AND DISPERSION OF BACTERIAL BIOFILMS WITH BENZIMIDAZOLE DERIVATIVES

(75) Inventors: Christian Melander, Raleigh, NC (US); Steven A. Rogers, Raleigh, NC (US); Robert W. Huigens, III, Wilmington, NC (US)

(73) Assignee: North Carolina State University, Raleigh, NC (US)

(*) Notice: Subject to any disclaimer, the term of this patent is extended or adjusted under 35 U.S.C. 154(b) by 169 days.

(21) Appl. No.: 13/377,388

(22) PCT Filed: Jun. 10, 2010

(86) PCT No.: PCT/US2010/038147
§ 371 (c)(1),
(2), (4) Date: Mar. 21, 2012

(87) PCT Pub. No.: WO2010/144686
PCT Pub. Date: Dec. 16, 2010

(65) Prior Publication Data
US 2012/0171129 A1     Jul. 5, 2012

Related U.S. Application Data

(60) Provisional application No. 61/185,780, filed on Jun. 10, 2009.

(51) Int. Cl.
*A61K 8/41* (2006.01)
*C07D 235/30* (2006.01)
(Continued)

(52) U.S. Cl.
CPC ............ *C07D 235/30* (2013.01); *C07D 401/04* (2013.01); *C07D 403/04* (2013.01); *Y10T 428/13* (2015.01); *Y10T 428/1393* (2015.01); *Y10T 428/23986* (2015.04); *Y10T 428/31678* (2015.04); *Y10T 428/31989* (2015.04)

(58) Field of Classification Search
CPC .................................................... A61K 8/411
See application file for complete search history.

(56) References Cited

U.S. PATENT DOCUMENTS

| | | | |
|---|---|---|---|
| 3,575,929 | A | 4/1971 | Jones |
| 4,514,382 | A | 4/1985 | Gaffar et al. |

(Continued)

FOREIGN PATENT DOCUMENTS

| | | |
|---|---|---|
| WO | WO 03/039529 A1 | 5/2003 |
| WO | WO 2004/047769 A2 | 6/2004 |

(Continued)

OTHER PUBLICATIONS

Ahmed, M. U., Frye, E.B., Degenhardt, T. P., Thorpe, S. R., and Baynes, J. W., "N$^\epsilon$(Carboxyethyl)lysine, a product of the chemical modification of proteins by methylglyoxal, increases with age in human lens proteins", Biochem. J. 324:565-570 (1997).

(Continued)

*Primary Examiner* — Benjamin Packard
(74) *Attorney, Agent, or Firm* — Myers Bigel Sibley & Sajovec, P.A.

(57) ABSTRACT

Disclosure is provided for benzimidazole derivative compounds that prevent, remove and/or inhibit the formation of biofilms, compositions including these compounds, devices including these compounds, and methods of using the same.

47 Claims, 10 Drawing Sheets

(51) Int. Cl.
*C07D 401/04* (2006.01)
*C07D 403/04* (2006.01)

(56) References Cited

U.S. PATENT DOCUMENTS

| | | | |
|---|---|---|---|
| 4,665,192 A | 5/1987 | Cerami | |
| 4,758,583 A | 7/1988 | Cerami et al. | |
| 4,983,604 A | 1/1991 | Ulrich et al. | |
| 5,128,360 A | 7/1992 | Cerami et al. | |
| 5,238,963 A | 8/1993 | Cerami et al. | |
| 5,358,960 A | 10/1994 | Ulrich et al. | |
| 5,476,849 A | 12/1995 | Ulrich et al. | |
| 5,534,540 A | 7/1996 | Ulrich et al. | |
| 5,656,261 A | 8/1997 | Cerami et al. | |
| 5,670,055 A | 9/1997 | Yu et al. | |
| 5,814,668 A | 9/1998 | Whittemore et al. | |
| 5,834,411 A | 11/1998 | Bolkan et al. | |
| 6,121,300 A | 9/2000 | Wagle et al. | |
| 6,143,774 A | 11/2000 | Heckmann et al. | |
| 6,338,904 B1 | 1/2002 | Patnaik et al. | |
| 6,699,994 B1 * | 3/2004 | Babu et al. | 546/306 |
| 6,790,859 B2 | 9/2004 | Wagle et al. | |
| 7,087,661 B1 | 8/2006 | Alberte et al. | |
| 7,132,567 B2 | 11/2006 | Alberte et al. | |
| 7,160,879 B2 | 1/2007 | DeSimone et al. | |
| 7,514,458 B2 | 4/2009 | Cogan et al. | |
| 7,897,631 B2 | 3/2011 | Melander et al. | |
| 7,906,544 B2 | 3/2011 | Melander et al. | |
| 2003/0171421 A1 | 9/2003 | Davies et al. | |
| 2003/0229000 A1 | 12/2003 | Merritt et al. | |
| 2004/0024037 A1 | 2/2004 | Ryu et al. | |
| 2004/0249441 A1 | 12/2004 | Miller et al. | |
| 2005/0161859 A1 | 7/2005 | Miller et al. | |
| 2006/0018945 A1 | 1/2006 | Britigan et al. | |
| 2006/0228384 A1 | 10/2006 | Eldridge | |
| 2006/0276468 A1 | 12/2006 | Blow | |
| 2007/0231291 A1 | 10/2007 | Huang et al. | |
| 2008/0181923 A1 | 7/2008 | Melander et al. | |
| 2009/0143230 A1 | 6/2009 | Melander et al. | |
| 2009/0263438 A1 | 10/2009 | Melander et al. | |
| 2009/0270475 A1 | 10/2009 | Melander et al. | |
| 2011/0117158 A1 | 5/2011 | Melander et al. | |
| 2011/0150819 A1 | 6/2011 | Melander et al. | |
| 2011/0294668 A1 | 12/2011 | Melander et al. | |

FOREIGN PATENT DOCUMENTS

| | | |
|---|---|---|
| WO | WO 2004047769 A2 * | 6/2004 |
| WO | WO 2005/012263 A1 | 2/2005 |
| WO | WO 2007/056330 A1 | 5/2007 |
| WO | WO 2010/077603 A1 | 7/2010 |
| WO | WO 2012/006276 A1 | 1/2012 |
| WO | WO 2012/030986 A2 | 3/2012 |
| WO | WO 2012/058531 A1 | 5/2012 |

OTHER PUBLICATIONS

Al-Abed, Y., Mitsuhashi, T., Li, H., Lawson, J. A., Fitzgerald, G. A., Founds, H., Donnelly, T., Cerami, A., Ulrich, P., and Bucala, R., "Inhibition of advanced glycation endproduct formation by acetaldehyde: Role in the cardioprotective effect of ethanol", Proc. Natl. Acad. Sci., USA, 96:2385-2390 (1999).
Alteon Inc. "Alteon's ALT-711 reduces diabetes-associated cardiac abnormalities", PRNewswire (2003). Retrieved Apr. 30, 2012, 3 pages.
Aurora Fine Chemicals Ltd. Search results 4-(4-butylphenyl)-1H-imidazol-2-amine. Retrieved Aug. 19, 2011, 3 pp.
Avery S. Slime-fighting molecule may rearm antibiotics. newsobserver.com. The News and Observer. Raleigh, NC. Apr. 22, 2009: 2 pp.
Ballard TE et al. Antibiofilm activity of a diverse oroidin library generated through reductive acylation. J. Org. Chem. 2009; 74(4): 1755-1758.
Ballard TE et al. Synthesis and antibiofilm activity of a second-generation reverse-amide oroidin library: a structure-activity relationship study. Chemistry. 2008; 14(34): 10745-61. Abstract only.
Beyer, H., Hetzheim, A., Honack, H., Ling, D. and Ply, T. "Synthesen neuer Imizazol-Derivate", Chem. Ber. 101, 3151-3162 (1968).
Breckle G et al. Document No. 139:164905 retrieved from CAPLUS on Jan. 3, 2010.
Burtles, R. and Pyman, F. L., "CCLXXII.-2-Amino-4:5-dimethylglyoxaline", J. Chem Soc. [London] 127, 2012 (1925).
Canadian Paedriatric Society. Antimicrobial products in the home: The evolving problem of antibiotic resistance. Paediatrics & Child Health. 2006; 11(3): 169-173.
Casalinuovo IA et al. Fluconazole resistance in *Candida albicans*: a review of mechanisms. European Review for Medical and Pharmacological Sciences. 2004; 8(2): 69-77.
Cavalleri B et al. Synthesis and biological activity of some 2-aminoimidazoles. Arzneim.-Forsch./Drug Res. 1977; 27(1): 1889-95.
Chang, J. C. F., Ulrich, P. C., Bucala, and Cerami, A., "Detection of an advanced glycosylation product bound to protein in situ", J. Biol. Chem. 260:7970-7974 (1985).
Eble et al., "Nonenzymatic glucosylation and glucose-dependent cross-linking of protein", J. Biol. Chem. 258:9406-9412 (1983).
Ermolat'ev DS and Van Der Eycken EV. A divergent synthesis of substituted 2-aminoimidazoles from 2-aminopyrimidines. Journal of Organic Chemistry. 2008; 73(17): 6691-6697.
Ermolat'ev DS et al. Concise and diversity-oriented route toward polysubstituted 2-aminoimidazole alkaloids and their analogues. Angew. Chem. 2010; 122: 9655-9658.
Ettmayer P et al. Lessons learned from marketed and investigational prodrugs. Journal of Medicinal Chemistry. May 6, 2004; 47(10): 2394-2404.
Finn FM and Hofmann K. Document No. 62:66837 retrieved from CAPLUS on Jan. 3, 2010.
Fishing for seafood safety. Scope. North Carolina State University College of Physical and Mathematical Sciences. Fall 2007: p. 11.
Foley L. and Büchi G. Biomimetic synthesis of dibromophakellin. J. Am. Chem. Soc. (1982), vol. 104, pp. 1776-1777.
Galvin F. Marine inspiration for biofilm break up. Chemical Biology. RCS Publishing. Mar. 5, 2008: 2 pp.
Ginsburg I. The role of bacteriolysis in the pathophysiology of inflammation, infection and post-infectious sequelae. APMIS. 2002; 110: 753-770.
Hayase, F., Nagaraj, R. H., Miyata, S., Njoroge, F.G., and Monnier, V. M., "Aging of proteins: immunological detection of a glucose-derived pyrrole formed during Maillard reaction in vivo", J. Biol. Chem. 263:3758-3764 (1989).
Hetzheim, A., Peters, O., and Beyer, H., "Uber die Ringumwandlung von 2-amino-3-phenacyl-1,3,4-oxadiazoliumhalogeniden mit Aminen zu 1,2-diamino-imidazol-derivaten", Chem. Ber. 100:3418-3426 (1967).
Hoffmann H and Lindel T. Synthesis of the pyrrole-imidazolealkaloids. Synthesis. 2003; 12: 1753-1783.
Huigens III R.W., et al. Inhibition of Pseudomonas aeruginosa biofilm formation with bromoageliferin analogues. J. Am. Chem. Soc. (2007), vol. 129, pp. 6966-6967.
Huigens III RW et al. The chemical synthesis and antibiotic activity of a diverse library of 2-aminobenzimidazole small molecules against MRSA and multidrug-resistant A. baumannii. Bioorganic & Medicinal Chemistry. 2010; vol. 18:663-674.
Huigens RW 3rd et al. Control of bacterial biofilms with marine alkaloid derivatives. Molecular BioSystems. 2008; 4: 614-621.
Huigens RW 3rd et al. Inhibition of *Acinetobacter baumannii*, *Staphylococcus aureus* and *Pseudomonas aeruginosa* biofilm formation with a class of TAGE-triazole conjugates. Org. Biomol. Chem. 2009; 7: 794-802.
International Search Report and Written Opinion for PCT/US08/01045, dated May 9, 2008.
International Search Report and Written Opinion, PCT/US09/02101, mailed Jul. 13, 2009.
International Search Report and Written Opinion, PCT/US09/02446, mailed Aug. 31, 2009.

(56) References Cited

OTHER PUBLICATIONS

Kelly SR et al. Effects of Caribbean sponge extracts on bacterial attachment. Aquatic Microbial Ecology. Mar. 13, 2003; 31: 175-182.
Kelly SR et al. Effects of Caribbean sponge secondary metabolites on bacterial colonization. Aquatic Microbial Ecology. Sep. 6, 2005; 40: 191-203.
Kirk KL et al. Document No. 80:15172 retrieved from CAPLUS on Jan. 3, 2010.
Lata et al. Analysis and prediction of antibacterial peptides. BMC Bioinformatics, 2007; 8: 263-272.
Lo, T. W. C., Westwood, M. E., McLellan, A. C., Selwood, T., and Thornalley, R. J., "Binding and modification of proteins by methylglyoxal under physiological conditions", J. Biol, Chem. 269:32299-32305 (1994).
Lydersen K. Scientists learning to target bacteria where they live. washingtonpost.com. The Washington Post. Mar. 9, 2009; A05: 3 pp.
Melander C et al. Evaluation of dihydrooroidin as an antifouling additive in marine paint. International Biodeterioration & Biodegradation. 2009; 53: 529-532.
Monnier, V. M., and Cerami, A., "Nonenzymatic browning in vivo: possible process for aging of long-lived proteins", Science 211:491-493 (1981).
Mourabit A. A. and Potier P. Sponge's molecular diversity through the ambivalent reactivity of 2-aminoimidazole: a universal chemical pathway to the oroidin-based pyrrole-imidazole alkaloids and their palau'amine congeners. Eur. J. Org. Chem. (2001), pp. 237-243.
Musk Jr. D.J. and Hergenrother P.J. Chemical countermeasures for the control of bacterial biofilms: effective compounds and promising targets. Current Medicinal Chemistry (2006), vol. 13, pp. 2163-2177.
Nagaraj, R. H., Shipanova, I. N., and Faust, F. M., "Protein cross-linking by the Maillard reaction", J. Biol. Chem. 271:19338-19345 (1996).
Oimomi, M., Igaki, N., Sakai, M., Ohara, T., Baba, S., and Kato, H., "The effects of aminoguanidine on 3-deoxyglucosone in the Maillard reaction", Agric. Biol. Chem., 53:1727-1728 (1989).
Otava Chemicals. Building Blocks search our compounds by structure on-line. Retrieved Aug. 22, 2011, 2 pp.
Paul, R. G., Avery, N. C., Slatter, D. A., Sims, T. J., and Bailey, A. J., "Isolation and characterization of advanced glycation end products derived from the in vitro reaction of ribose and collagen", Biochem., J. 330:1241-1248 (1998).
Pyl, T., Lahmer, H., and Beyer, "Over 2-imidazoles and their Phenylhydrazono benzidinartige rearrangement" Chem. Ber., p. 3217-3223 (1961).
Rautio J et al. Prodrugs: design and clinical applications. Nature Reviews. Mar. 2008; 7: 255-270.
Reed, Catherine Suzanne. The Design and Synthesis of 2-Aminoimidazole Biofilm Modulators. A thesis submitted to the Graduate Faculty of North Carolina State University in partial fulfillment of the requirements for the Degree of Master of Science. Aug. 4, 2010. 255 pages.
Rice LB. Unmet medical needs in antibacterial therapy. Biochemical Pharmacology. 2006; 71: 991-995.
Richards JJ and Melander C. Controlling bacterial biofilms. ChemBioChem, Epub ahead of print: Aug. 13, 2009; 9 pp.
Richards JJ and Melander C. Synthesis of a 2-aminoimidazole library for antibiofilm screening utilizing the Sonogashira reaction. J. Org. Chem. 2008; 73(13): 5191-5193.
Richards JJ et al. Amide isosteres of oroidin: assessment of antibiofilm activity and *C. elegans* toxicity. Journal of Medicinal Chemistry. 2009; 52(15): 4582-4585.
Richards JJ et al. Effects of N-pyrrole substitution on the anti-biofilm activities of oroidin derivatives against Acinetobacter baumannii. Bioorganic & Medicinal Chemistry Letters. 2008; 18: 4325-4327.
Richards JJ et al. Inhibition and dispersion of proteobacterial biofilms. Chem. Comm. 2008; 1698-1700.
Richards JJ et al. Inhibition and dispersion of Pseudomonas aeruginosa biofilms with reverse amide 2-aminoimidazole oroidin analogues. Organic & Biomolecular Chemistry. Apr. 21, 2008; 6(8): 1301-1512.
Richards JJ et al. Synthesis and screening of an oroidin library against Pseudomonas aeruginosa biofilms. ChemBioChem. 2008; 9: 1267-1279.
Rogers SA and Melander C. Construction and screening of a 2-aminoimidazole library identifies a small molecule capable of inhibiting and dispersing bacterial biofilms across order, class, and phylum. Angew. Chem. Int. Ed. 2008; 47: 5229-5231.
Rogers SA et al. A 2-aminobenzimidazole that inhibits and disperses gram-positive biofilms through a zinc-dependent mechanism. J. Am. Chem. Soc. 2009; 131(29): 9868-9869.
Rogers SA et al. Chemical synthesis and biological screening of 2-aminoimidazole-based bacterial and fungal antibiofilm agents. Chembiochem. Feb. 2010; 11: 396-410.
Rogers SA et al. Synergistic effects between conventional antibiotics and 2-aminoimidazole-derived antibiofilm agents. Antimicrob. Agents Chemother. Mar. 8, 2010: 1-34.
Rogers SA et al. Tandem dispersion and killing of bacteria from a biofilm. Organic & Biomolecular Chemistry. 2009; 7: 603-606.
Salvatori M et al. Versatile access to C-4 substituted 2-amino-1,3-azoles from hydropyridines in oxidative conditions. J. Org. Chem. 2005; 70: 8208-8211.
San George, R. C. and Hoberman, H. D., "Reaction of acetaldehyde with hemoglobin", J. Biol. Chem. 261:6811-6821 (1986).
Sell, D. R. and Monnier, V. M., "Structure elucidation of a senescence cross-link from human extracellular matrix", J. Biol. Chem. 264:21597-21602 (1989).
Shore D. College Profile: Dr. John Cavanagh shows that in scientific collaboration—as in a community of molecules—the product is more powerful than the sum of its parts. Perspectives Online. North Carolina State University. Summer 2007: 4 pp.
Smith DA. Do prodrugs deliver? Current Opinion in Drug Discovery & Development. 2007; 10(5): 550-559.
Soh CH et al. An efficient and expeditious synthesis of di- and monosubstituted 2-aminoimidazoles. Journal of Combinatorial Chemistry. 2008; 10(1): 118-122.
Steenackers HPL et al. Structure-activity relationship of 2-hydroxy-2-aryl-2,3-dihydro-imidazo[1,2-a]pyrimidinium salts and 2N-substituted 4(5)-aryl-2-amino-1H-imidazoles as inhibitors of biofilm formation by *Salmonella typhirmurium* and *Pseudomas aeruginosa*. Bioorganic & Medicinal Chemistry. Jun. 1, 2011; 19(11): 3462-3473 (Abstract only).
Steenackers HPL et al. Structure-activity relationship of 4(5)-aryl-2-amino-1H-imidazoles, N1-substituted 2-aminoimidazoles and imidazo[1,2-a]pyrimidinium salts as inhibitors of biofilm formation by *Salmonella typhimurium* and *Pseudomonas aeruginosa*. Journal of Medicinal Chemistry. 2011; 54(2): 472-484.
Stella VJ. Prodrugs as therapeutics. Expert Opinion of Therapeutic Patents. 2004; 14(3): 277-280.
Stokstad E. Sponging away antibiotic resistance. Findings. The Science Magazine News Blog. Feb. 14, 2009: 1 p.
Supplementary European Search Report, EP 08713290, Mar. 24, 2011.
Taking the Resistance out of drug-resistant infections. PhysOrg.com. Apr. 10, 2009: 2 pp.
Testa B. Prodrug research: futile or fertile? Biochemical Pharmacology. 2004; 68: 2097-2106.
Testa B. Prodrugs: bridging pharmacodynamic/pharmacokinetic gaps. Current Opinion in Chemical Biology. 2009; 13: 338-344.
Ulrich, P. and Cerami, A., "Protein glycation, diabetes, and aging", Endocrine Reviews, 56:1-22 (2001).
Vasan, S., Zhang, X., Zhang, X., Kapurniotu, A., Bernhagen, J., Teichberg, S., Basgen, J., Wagle, D., Shih, D., Terlecky, I., Bucala, Cerami, A., Egan, J., and Ulrich, P., "An agent cleaving glucose-derived protein crosslinks in vitro and in vivo", Nature 382:275-278 (1996).
Wang B et al. Drug delivery: principles and applications. 2005 John Wiley & Sons, Inc. Publication. Section 8.3, pp. 136-137.
Wolff ME et al. Burger's Medicinal Chemistry, 5th Ed., vol. 1, pp. 975-977, 1994.

(56) References Cited

OTHER PUBLICATIONS

Wolffenbuttel, B. H. R., Boulanger, C. M., Crijns, F. R. L., Huijberts, M. S. P., Poitevin, P., Swennen, G. N. M., Vasan, S.,.Egan, J. J., Ulrich, P., Cerami, A. and Levy, B. I., "Breakers of advanced glycation end products restore large artery properties in experimental diabetes", Proc. Natl. Acad. Sci., USA 95:4630-4634 (1998).

Yamada A. et al. Development of chemical substances regulating biofilm formation. Bull. Chem. Soc. Jpn. (1997), No. 70, pp. 3061-3069.

International Search Report and Written Opinion of the International Searching Authority corresponding to international application No. PCT/US10/38147 mailed Aug. 13, 2010.

* cited by examiner

INHIBITION AND DISPERSION OF BACTERIAL BIOFILMS WITH BENZIMIDAZOLE DERIVATIVES

RELATED APPLICATIONS

This application is a 35 U.S.C. §371 national phase entry of PCT Application PCT/US2010/038147, filed Jun. 10, 2010, and published in English on Dec. 16, 2010, as International Publication No. WO 2010/144686, and which claims the benefit under 35 U.S.C. §119(e) of U.S. Provisional Patent Application Ser. No. 61/185,780, filed Jun. 10, 2009, the disclosure of each of which is incorporated herein by reference in its entirety.

This application is related to U.S. application Ser. No. 12/020,112, filed Jan. 25, 2008, and published Jul. 31, 2008, as publication no. 2008/0181923, now issued as U.S. Pat. No. 7,906,544, the disclosure of which is incorporated herein by reference in its entirety.

FIELD OF THE INVENTION

This invention relates to compounds, compositions and methods useful for controlling biofilms and other microorganisms.

BACKGROUND OF THE INVENTION

Biofilms are complex communities of microorganisms that are commonly found on a variety of substrates or surfaces that are moist or submerged (Musk et al., *Curr. Med. Chem.*, 2006, 13, 2163; Donlan et al., *Clin. Microbiol. Rev.*, 2002, 15, 167). Though primarily populated by bacteria, biofilms can also contain many different individual types of microorganisms, e.g., bacteria, archaea, protozoa and algae. The formation of biofilms can be thought of as a developmental process in which a few free-swimming (planktonic) bacteria adhere to a solid surface and, in response to appropriate signals, initiate the formation of a complex sessile microcolony existing as a community of bacteria and other organisms. Bacteria within biofilms are usually embedded within a matrix, which can consist of protein, polysaccharide, nucleic acids, or combinations of these macromolecules. The matrix is a critical feature of the biofilm that protects the inhabiting organisms from antiseptics, microbicides, and host cells. It has been estimated that bacteria within biofilms are upwards of 1.000-fold more resistant to conventional antibiotics (Rasmussen et al., *Int. J. Med. Microbiol.*, 2006, 296, 149).

Biofilms play a significant role in infectious disease. It is estimated that biofilms account for between 50-80% of microbial infections in the body, and that the cost of these infections exceeds $1 billion annually. For example, persistent infections of indwelling medical devices remain a serious problem for patients, because eradication of these infections is virtually impossible. A few diseases in which biofilms have been implicated include endocarditis, otitis media, chronic prostatitis, periodontal disease, chronic urinary tract infections, and cystic fibrosis. The persistence of biofilm populations is linked to their inherent insensitivity to antiseptics, antibiotics, and other antimicrobial compounds or host cells.

Deleterious effects of biofilms are also found in non-medical settings. For example, biofilms are a major problem in the shipping industry. Biofilms form on and promote the corrosion of ship hulls and also increase the roughness of the hulls, increasing the drag on the ships and thereby increasing fuel costs. The biofilms can also promote the attachment of larger living structures, such as barnacles, to the hull. Fuel can account for half of the cost of marine shipping, and the loss in fuel efficiency due to biofilm formation is substantial. One method of controlling biofilms is to simply scrape the films off of the hulls. However, this method is costly and time-consuming, and can promote the spread of troublesome non-native species in shipping waters. Another method involves the use of antifouling coatings containing tin. However, tin-based coatings are now disfavored due to toxicity concerns.

Given the breadth of detrimental effects caused by bacterial biofilms, there has been an effort to develop small molecules that will inhibit their formation (Musk et al., *Curr. Med. Chem.*, 2006, 13, 2163). The underlying principle is that if bacteria can be maintained in the planktonic state, they will either not attach to a target surface and/or they can be killed by a lower dose of microbicide.

Despite the extent of biofilm driven problems, examples of structural scaffolds that inhibit biofilm formation are rare (Musk et al., *Curr. Med. Chem.*, 2006, 13, 2163). The few known examples include the homoserine lactones (Geske et al., *J. Am. Chem. Soc.*, 2005, 127, 12762), which are naturally-occurring bacterial signaling molecules that bacteria use in quorum sensing (Dong et al., *J, Microbiol.*, 2005, 43, 101; Nealson et al., *J. Bacteriol.*, 1970, 104, 313), brominated furanones isolated from the macroalga *Delisea pulchra* (Hentzer et al., *Microbiology-Sgm*, 2002, 148, 87), and ursene triterpenes from the plant *Diospyros dendo* (Hu et al., *J. Nat. Prod.*, 2006, 69, 118). While the focus has predominantly been on designing small molecules that inhibit the formation of biofilms, one of the more significant challenges is the development of a small molecule that disperses pre-formed biofilms. None of the small molecules noted above have been previously reported to disperse an existing biofilm.

In addition, bacteria have an unparalleled ability to overcome foreign chemical insult. For example, resistance to vancomycin, "the antibiotic of last resort," has become more prevalent, and strains of vancomycin-resistant *Staphylococcus aureus* have become a serious health risk. It has been predicted that it is simply a matter of time before different bacterial strains develop vancomycin resistance, and the safety net that vancomycin has provided for decades in antibiotic therapy will no longer be available. Therefore, the identification of chemical architectures useful to inhibit biofilm development is needed.

Because of their natural resistance to antibiotics, phagocytic cells, and other biocides, biofilms are difficult, if not impossible, to eradicate. Therefore, the identification of compounds that control biofilms is of critical need.

SUMMARY OF THE INVENTION

Provided herein are compounds of Formula (I):

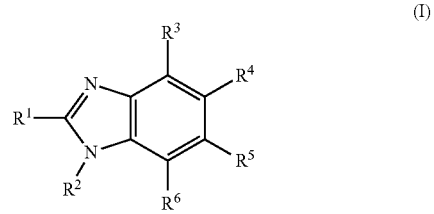

wherein:
$R^1$, $R^2$, $R^3$, $R^4$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (I), $R^1$ is a substituted amino, generally depicted by Formula (I)(a):

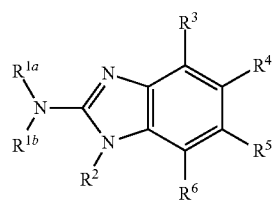

(I)(a)

wherein:
$R^{1a}$, $R^{1b}$, $R^2$, $R^3$, $R^4$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (I)(a), $R^{1a}$ and $R^{1b}$ are each H, generally depicted by Formula (I)(a)(i):

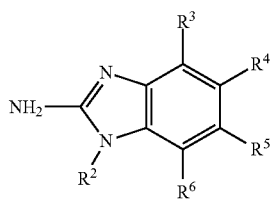

(I)(a)(i)

wherein:
$R^2$, $R^3$, $R^4$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, $R^2$, $R^3$, $R^5$ and $R^6$ are each independently H or alkyl (e.g., lower alkyl having from 1 to 5 or from 1 to 10 carbon atoms).

In some embodiments, the substituent at $R^4$ is substituted at least once with a halo and/or a carbonyl.

Also provided are compounds of Formula (II):

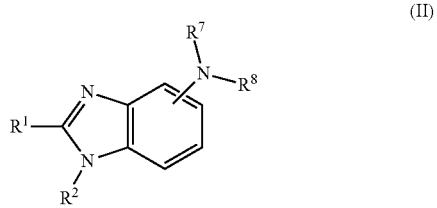

(II)

wherein:
$R^1$ and $R^2$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein $R^7$ and $R^8$ together form a ring;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II), $R^1$ is a substituted amino, generally depicted by Formula (II)(a):

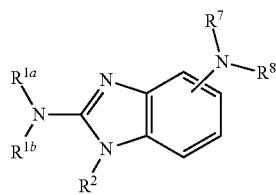

(II)(a)

wherein:
$R^{1a}$, $R^{1b}$ and $R^2$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein $R^7$ and $R^8$ together form a ring;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, $R^{1a}$, $R^{1b}$ and $R^2$ are each independently H or alkyl (e.g., lower alkyl having from 1 to 5 or from 1 to 10 carbon atoms).

In some embodiments of Formula (II)(a), $R^{1a}$ and $R^{1b}$ are each H, generally depicted by Formula (II)(a)(i):

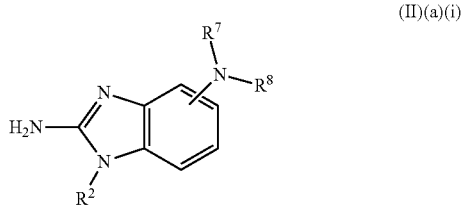

(II)(a)(i)

wherein:

$R^2$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein $R^7$ and $R^8$ together form a ring;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, $R^2$ is H or alkyl (e.g., lower alkyl having from 1 to 5 or from 1 to 10 carbon atoms).

In some embodiments of Formula (II)(a)(i), $R^7$ is acyl, generally depicted by Formula (II)(a)(i)(A):

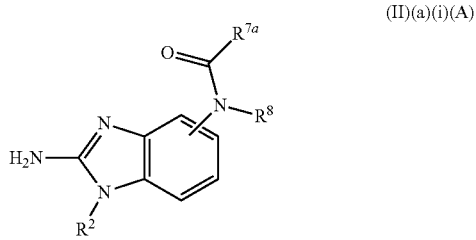

(II)(a)(i)(A)

wherein:

$R^2$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and $R^{7a}$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein $R^{7a}$ and $R^8$ together form a ring;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, $R^2$ is H or alkyl. In some embodiment, $R^8$ is H or alkyl. In some embodiments, $R^{7a}$ is alkyl, alkenyl, alkynyl. In some embodiments, $R^{7a}$ is aryl. In some embodiments, the group at $R^{7a}$ has a carboxy substitution. In some embodiments, the group at $R^{7a}$ has one or more halo substitutions.

In some embodiments of Formula (II)(a)(i), $R^7$ and $R^8$ are each acyl, generally depicted by Formula (II)(a)(i)(B):

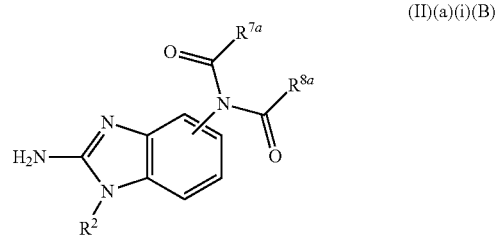

(II)(a)(i)(B)

wherein:

$R^2$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and $R^{7a}$ and $R^{8a}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein $R^{7a}$ and $R^{8a}$ together form a ring;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, $R^2$ is H or alkyl (e.g., lower alkyl having from 1 to 5 or from 1 to 10 carbon atoms).

Biofilm preventing, removing or inhibiting compositions are provided, which include a carrier and an effective amount of a compound disclosed herein. In some embodiments, the composition is a dentifrice composition that promotes dental hygiene by preventing, reducing, inhibiting or removing a biofilm. In some embodiments, the dentifrice composition comprises a toothpaste, mouthwash, chewing gum, dental floss, or dental cream.

Compositions are also provided that include a compound disclosed herein in a pharmaceutically acceptable carrier.

Compositions are further provided that include a compound disclosed herein covalently coupled to a substrate. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate (The Diller Corporation, Cincinnati, Ohio). In some embodiments, the substrate includes shower curtains or liners, upholstery, laundry, and carpeting. In some embodiments, the substrate includes a ship hull or a portion thereof. In some embodiments, the substrate includes a food contact surface.

Biofilm preventing, removing or inhibiting coating compositions are provided, including: (a) a film-forming resin; (b) a solvent that disperses said resin; (c) an effective amount of the compounds or compositions disclosed herein, wherein said effective amount prevents or inhibits the growth of a biofilm thereon; and (d) optionally, at least one pigment. In some embodiments, the compound is covalently coupled to the resin. In some embodiments, the resin includes a polymeric material.

Substrates coated with coating composition disclosed herein are also provided. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate. In some embodiments, the substrate includes shower curtains or liners, upholstery, laundry, and carpeting. In some embodiments, the substrate includes a ship hull or a portion thereof. In some embodiments, the substrate includes a food contact surface.

Methods of controlling biofilm formation on a substrate are provided, including the step of contacting the substrate with a compound and/or composition disclosed herein in an amount effective to inhibit biofilm formation. In some embodiments, controlling biofilm formation includes clearing a preformed biofilm from said substrate by administering an effective amount of the compound and/or composition disclosed herein to said substrate, wherein said effective amount will reduce the amount of said biofilm on said substrate. In some embodiments, the substrate may include a drainpipe, glaze ceramic, porcelain, glass, metal, wood, chrome, plastic, vinyl, and Formica® brand laminate. In some embodiments, the substrate may include a food product (e.g., seafood). In some embodiments, the biofilm includes Gram-negative bacteria.

Methods for treating and/or preventing a bacterial infection (e.g., chronic bacterial infection) in a subject in need thereof are provided, including administering to said subject a compound and/or composition disclosed herein in an amount effective to inhibit, reduce, or remove a biofilm component of said bacterial infection. The bacterial infection may include urinary tract infection, gastritis, respiratory infection, cystitis, pyelonephritis, osteomyelitis, bacteremia, skin infection, rosacea, acne, chronic wound infection, infectious kidney stones, bacterial endocarditis, and sinus infection.

Also provided are medical devices, including (a) a medical device substrate; and (b) an effective amount of a compound disclosed herein, either coating the substrate, or incorporated into the substrate, wherein said effective amount prevents or inhibits the growth of a biofilm thereon. In some embodiments, the medical device substrate may include stents, fasteners, ports, catheters, scaffolds and grafts. In some embodiments, the compound is covalently coupled to said substrate.

Compounds and/or compositions for use in a method to control a biofilm are further provided. Also provided is the use of compounds and/or compositions disclosed herein for the preparation of a medicament for the treatment and/or prevention of a bacterial infection (e.g., chronic bacterial infection).

DETAILED DESCRIPTION OF EMBODIMENTS

Figure 1A:
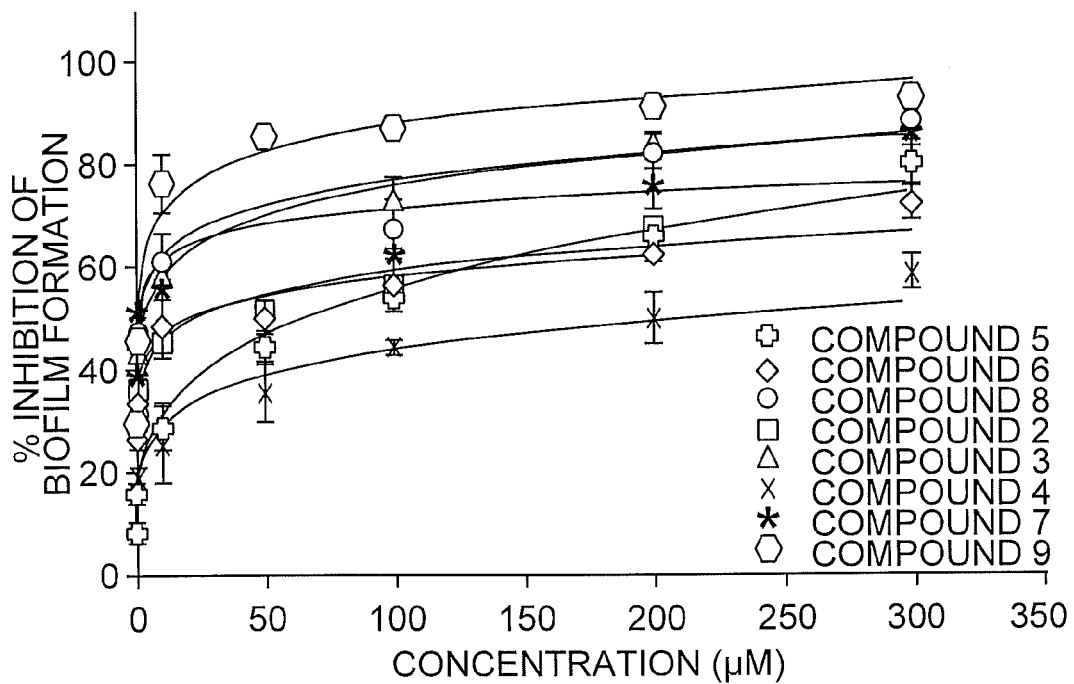
FIG. 1A-1B. Inhibitory effect of compounds on *E. faecium* biofilim formation.
Figure 1B:
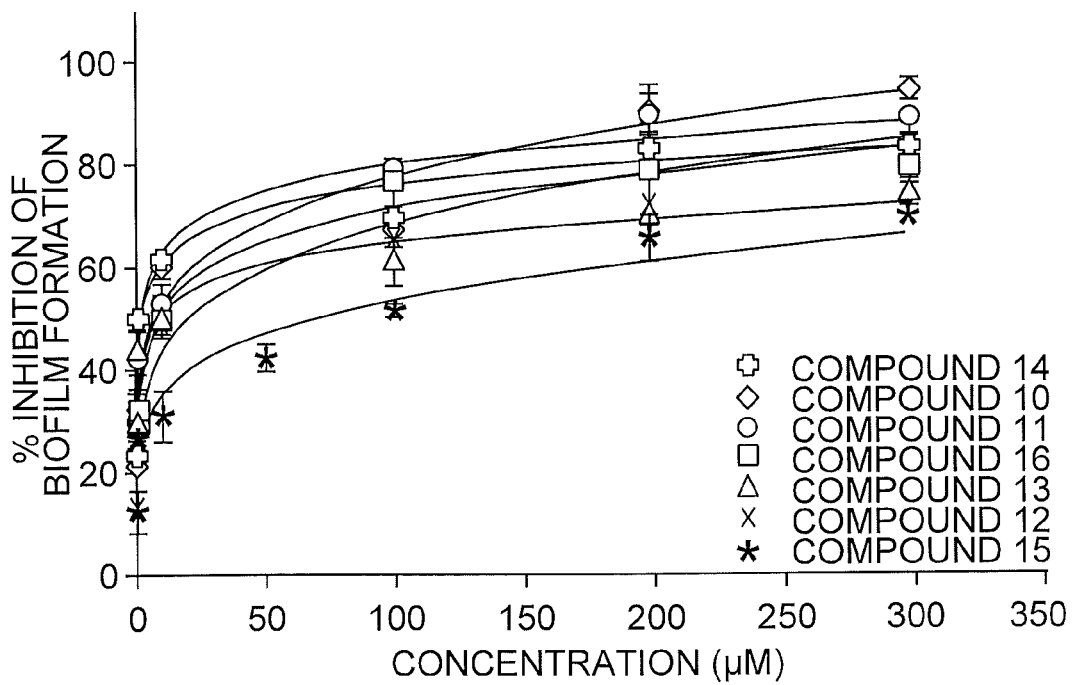
Figure 2A:
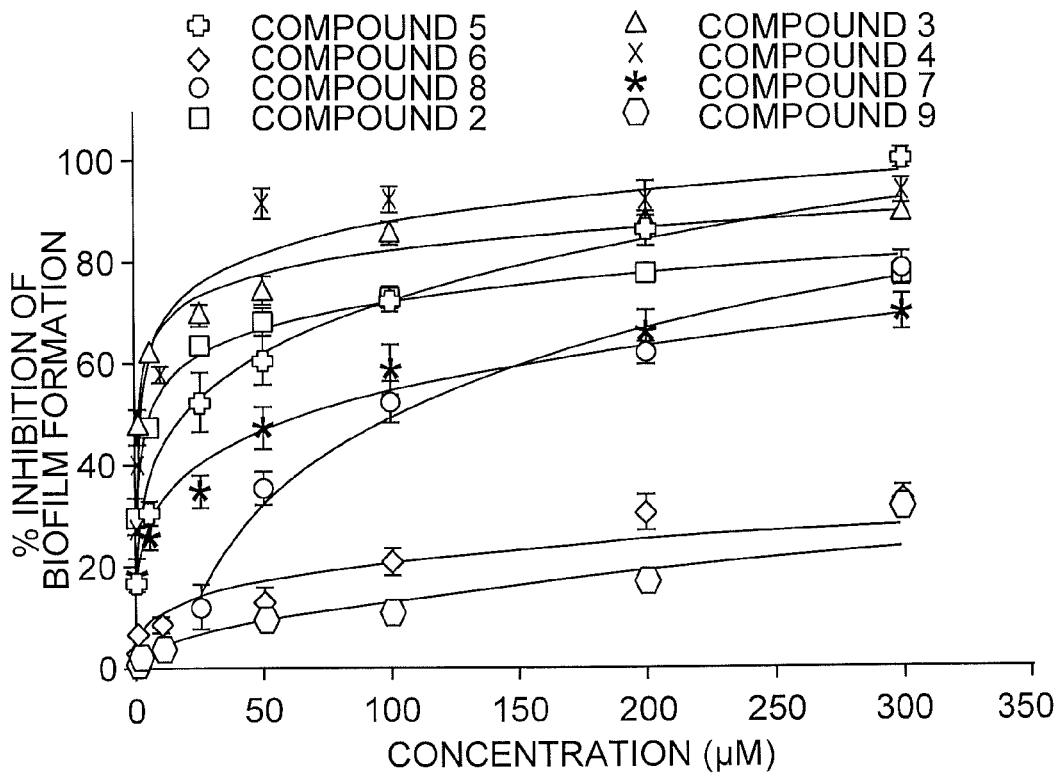
FIG. 2A-2B. Inhibitory effect of compounds on MRSA biofilm formation.
Figure 2B:
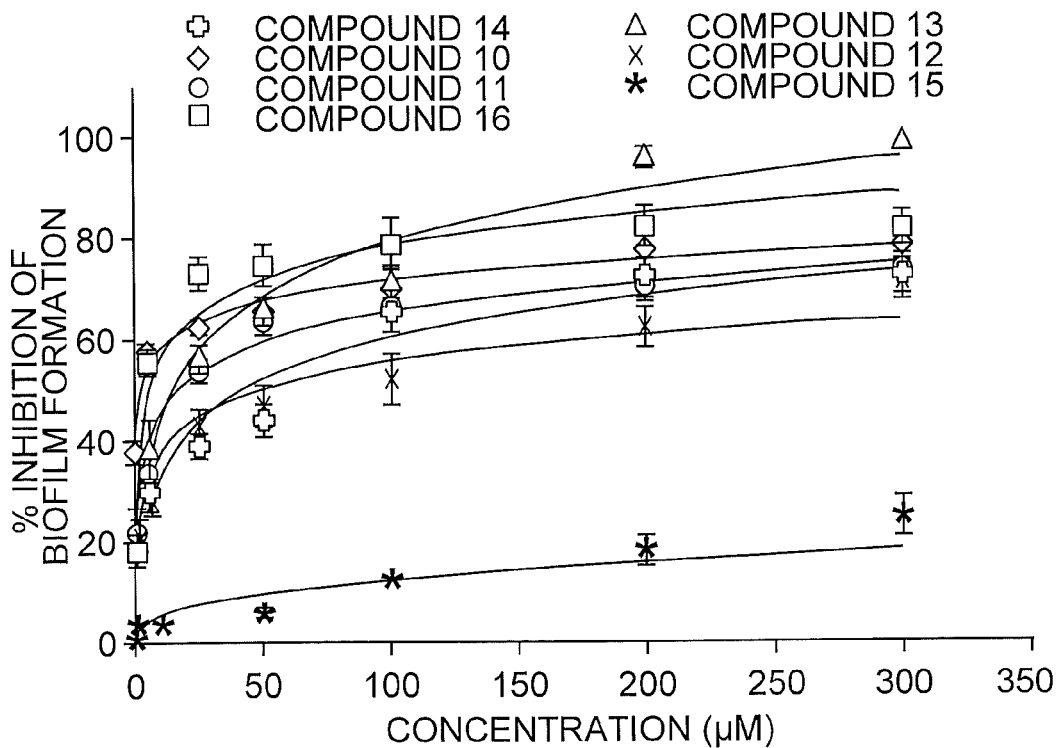
Figure 3A:
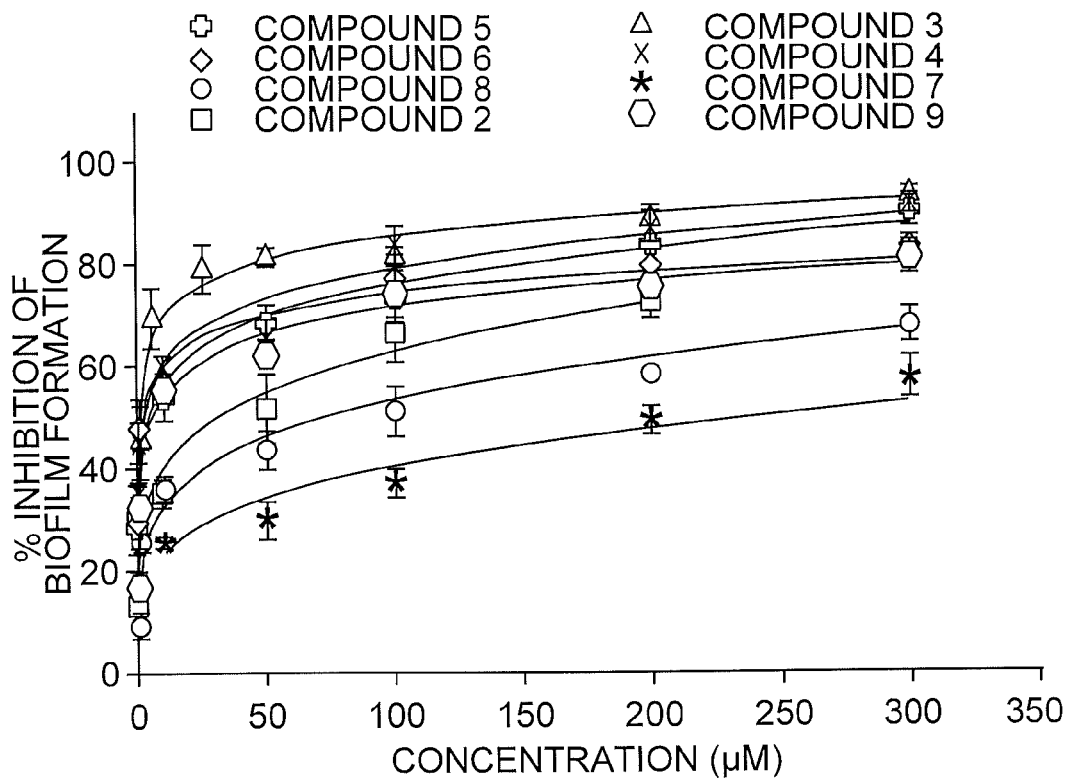
FIG. 3A-3B. Inhibitory effect of compounds on *S. epidermidis* biofilm formation.
Figure 3B:
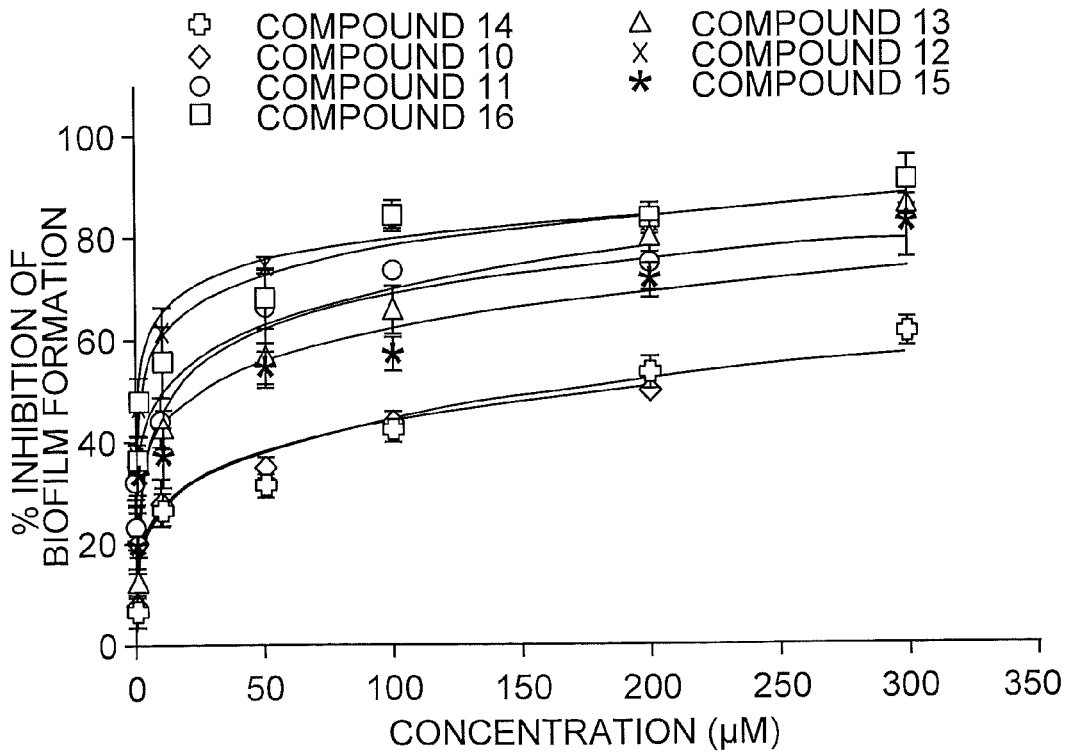
Figure 4A:
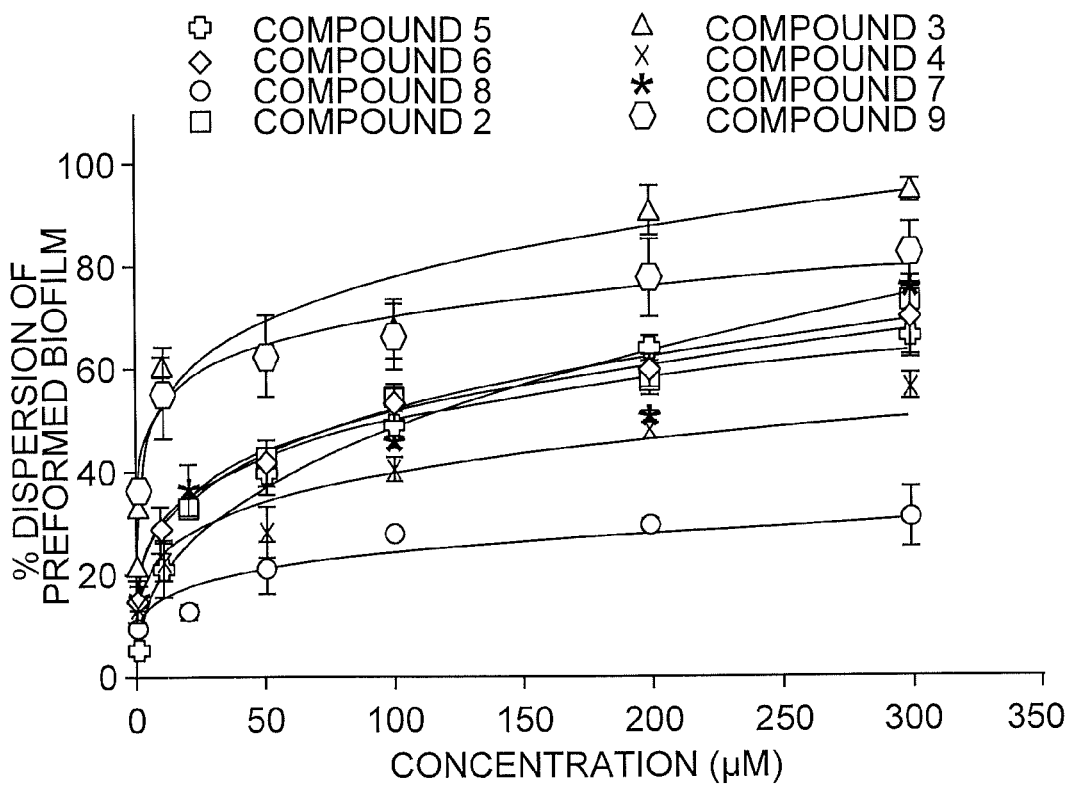
FIG. 4A-4B. Dispersion effect of compounds on *E. faecium* preformed biofilim.
Figure 4B:
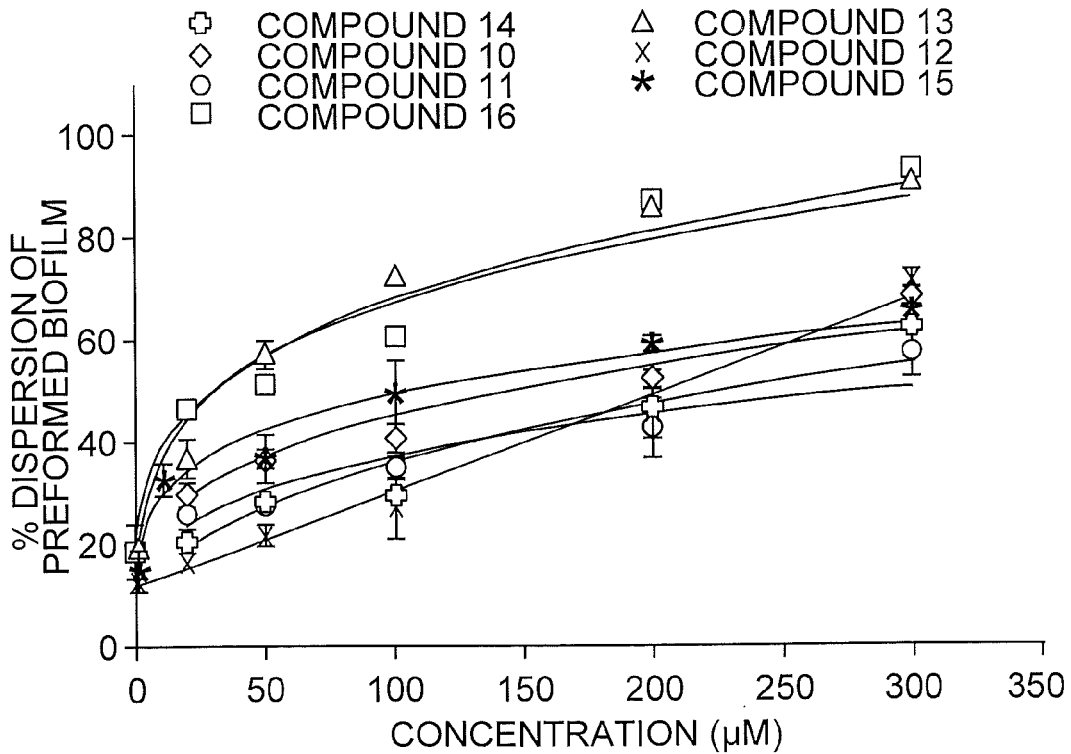
Figure 5A:
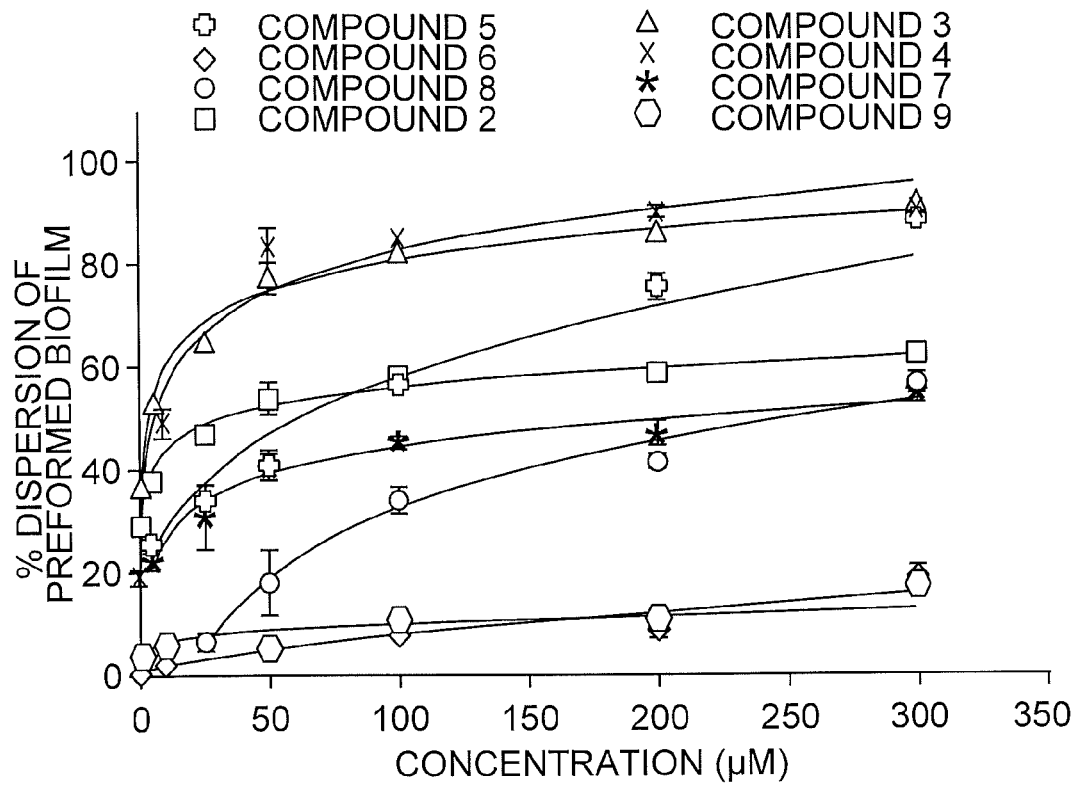
FIG. 5A-5B. Dispersion effect of compounds on MRSA preformed biofilm.
Figure 5B:
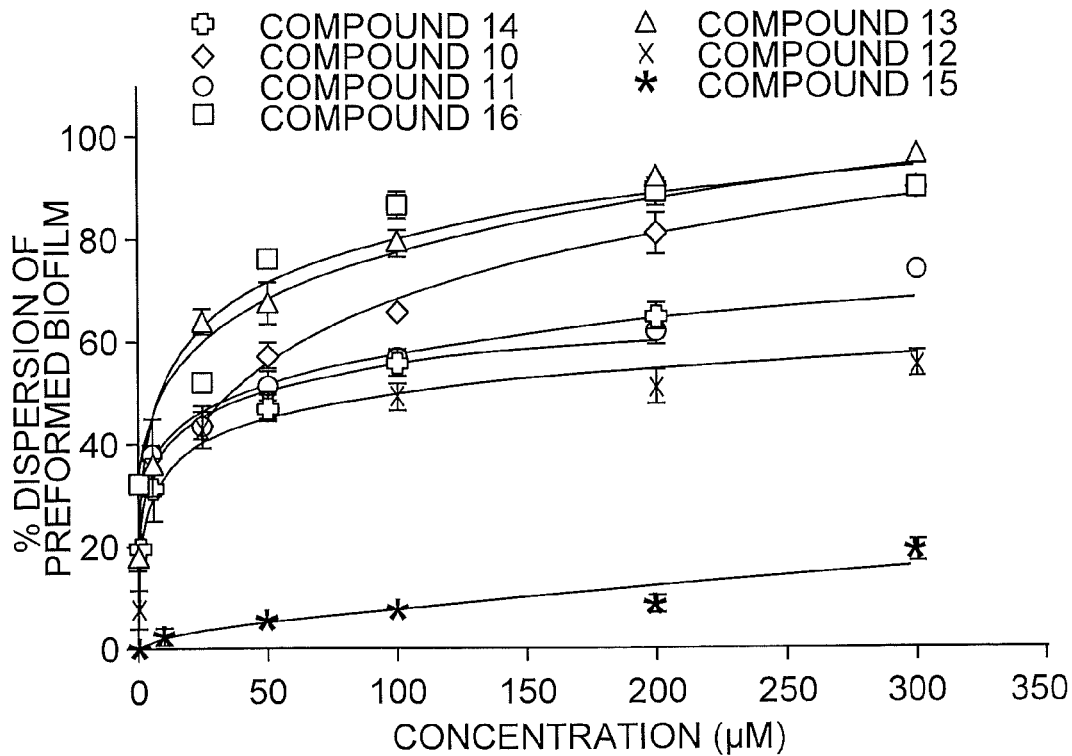
Figure 6A:
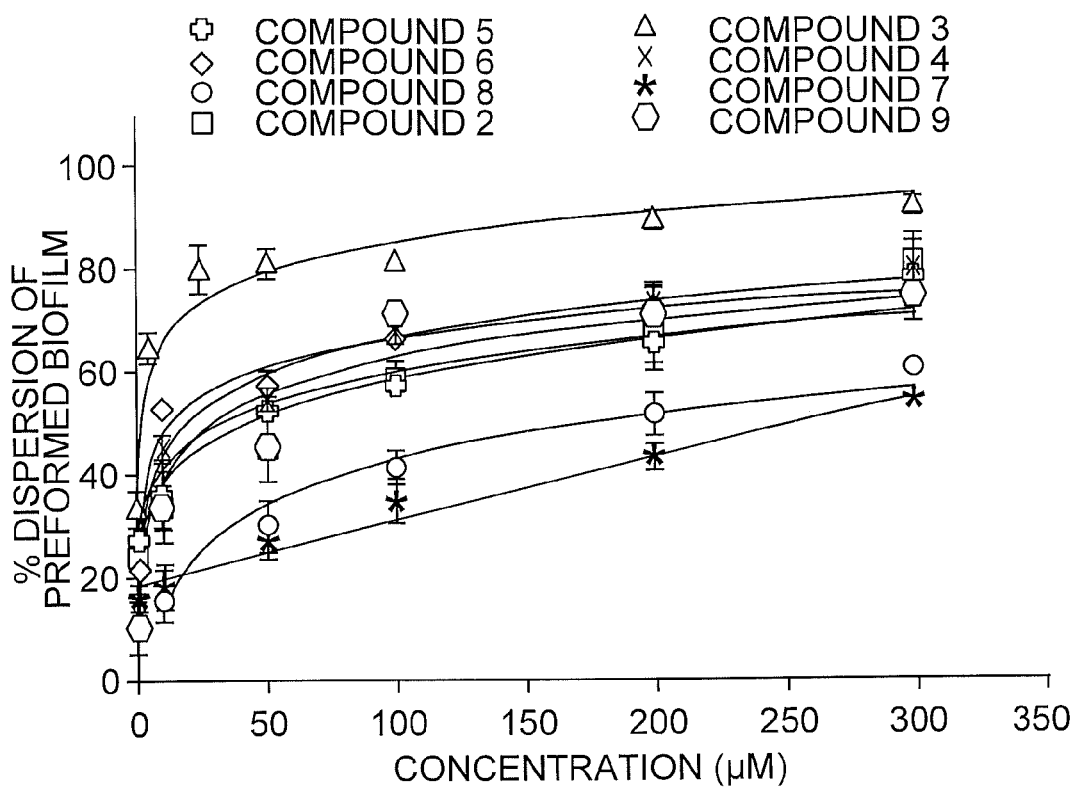
FIG. 6A-6B. Dispersion effect of compounds on *S. epidermidis* preformed biofilm.
Figure 6B:
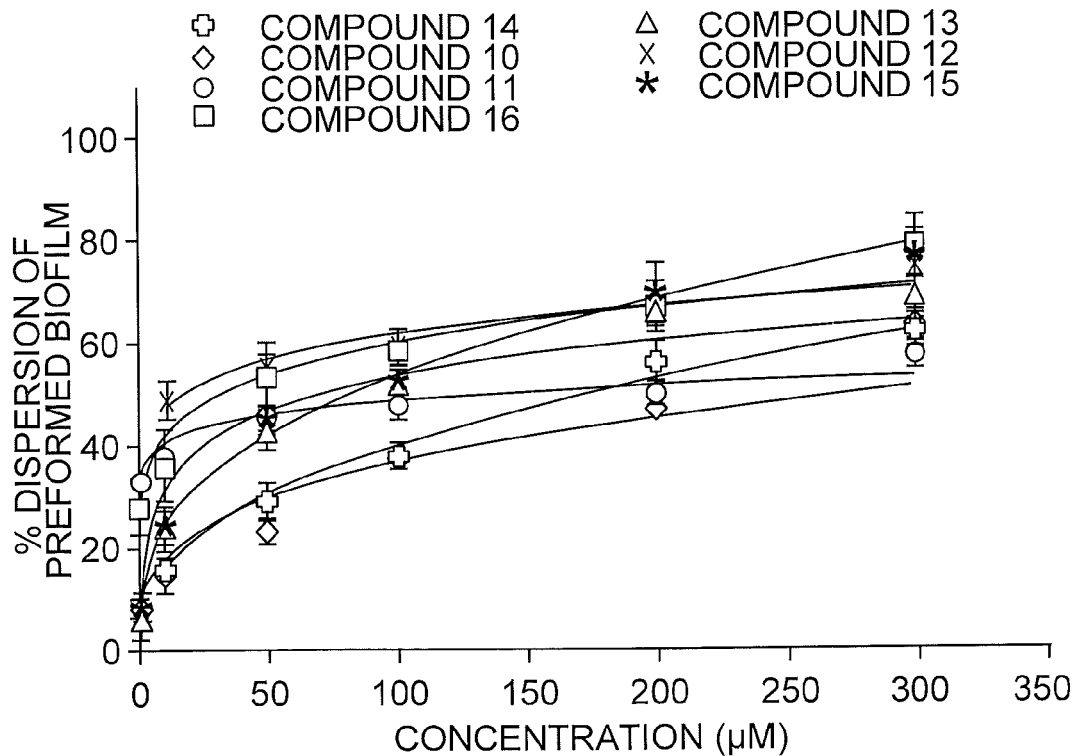
Figure 7A:
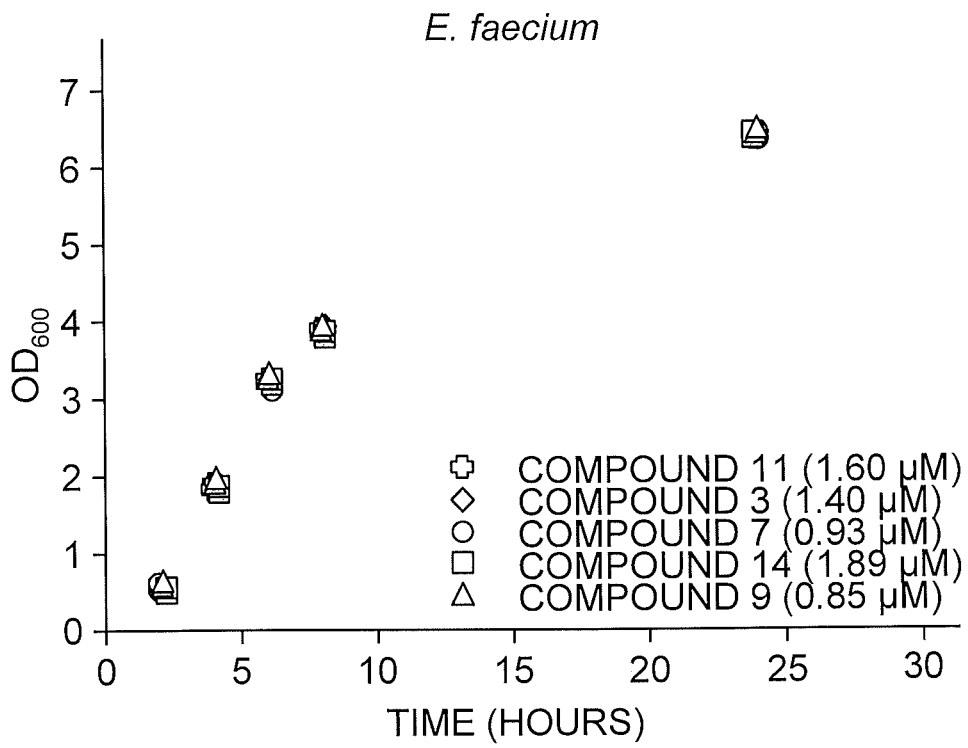
FIG. 7A-7C. Effect of compounds on *E. faecium*, MRSA and *S. epidermidis* planktonic viability as measured by growth curve analysis.
Figure 7B:
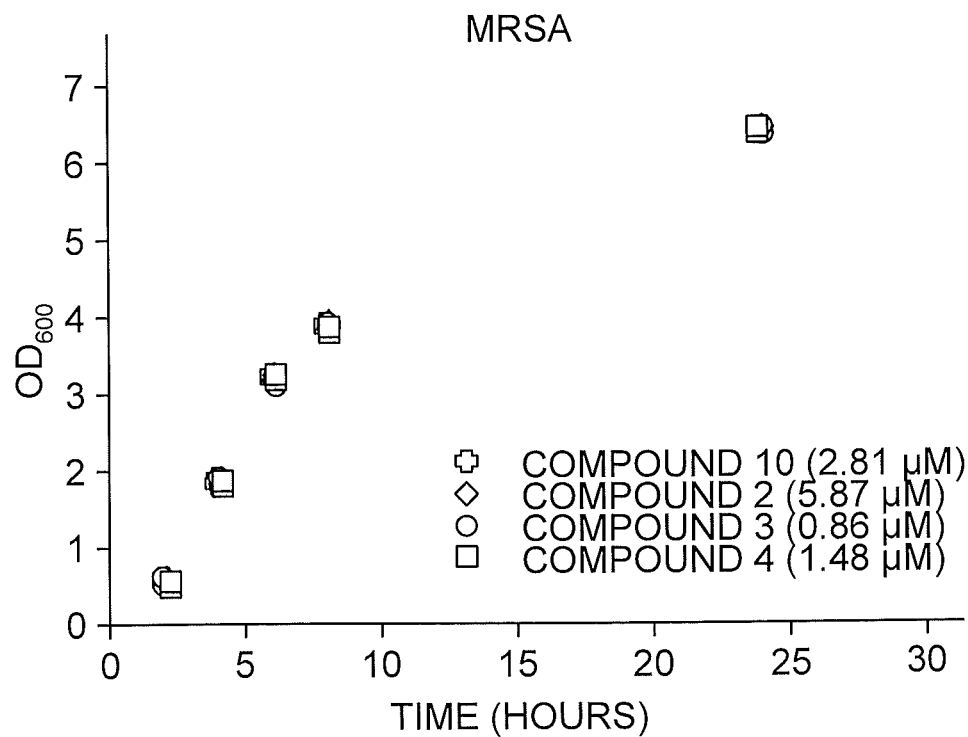
Figure 7C:
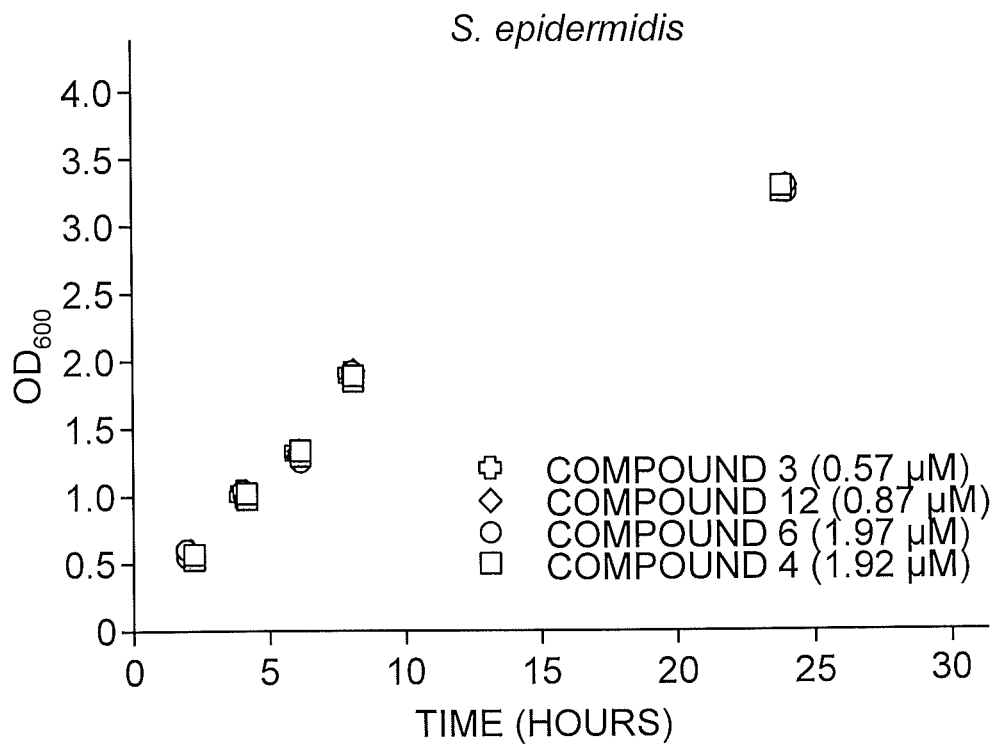
Figure 8A:
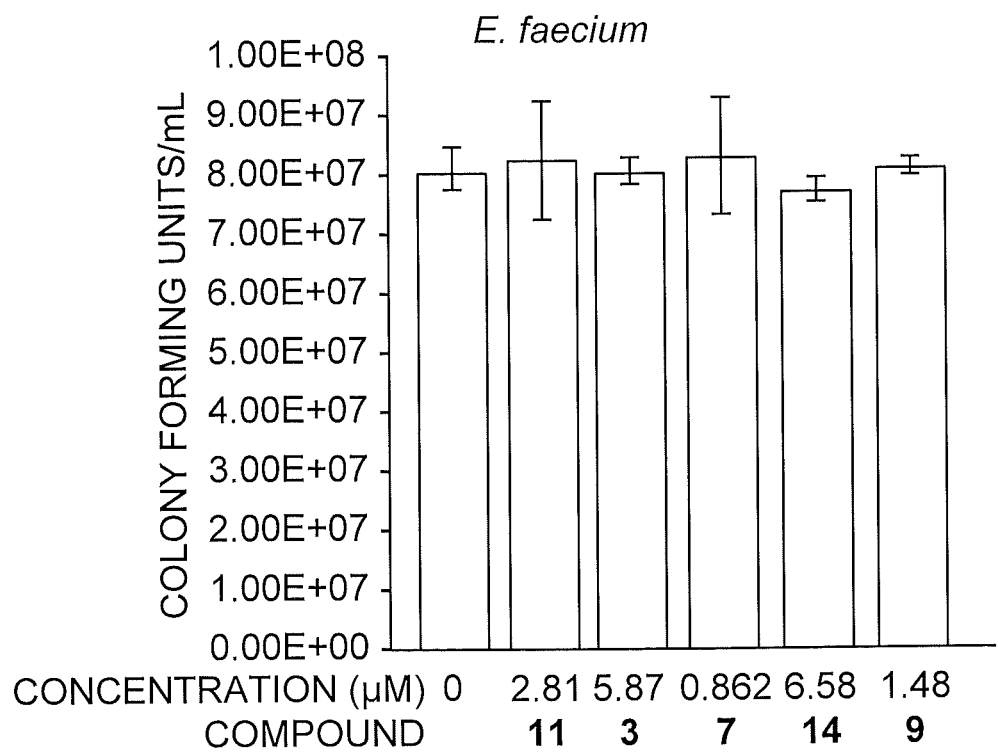
FIG. 8A-8C. Colony counts to determine the effect of compounds on *E. faecium*, MRSA and *S. epidermidis* planktonic viability.
Figure 8B:
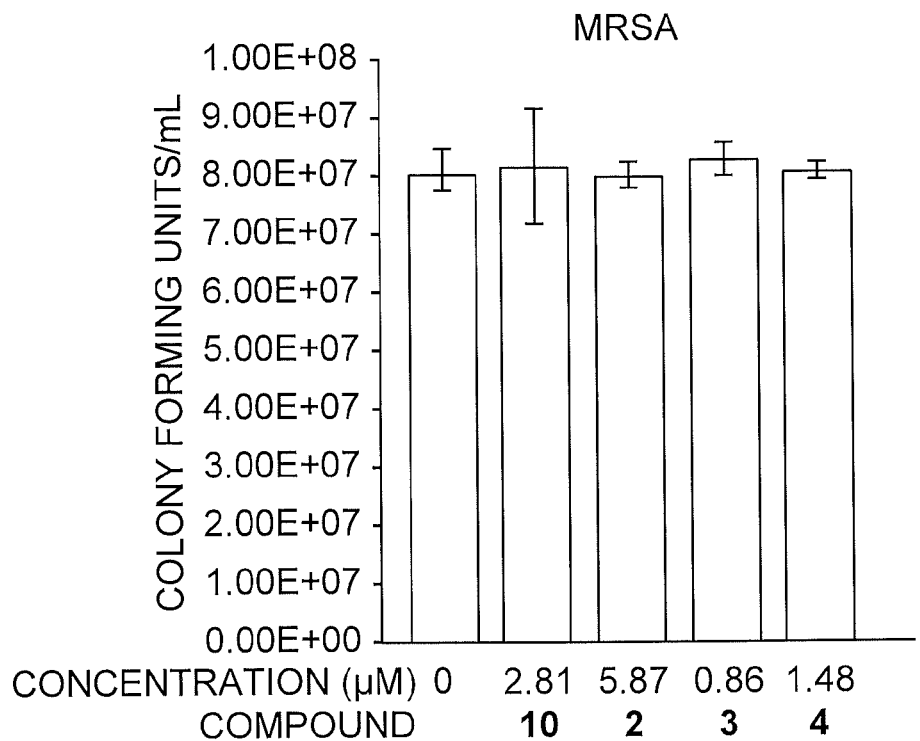
Figure 8C:
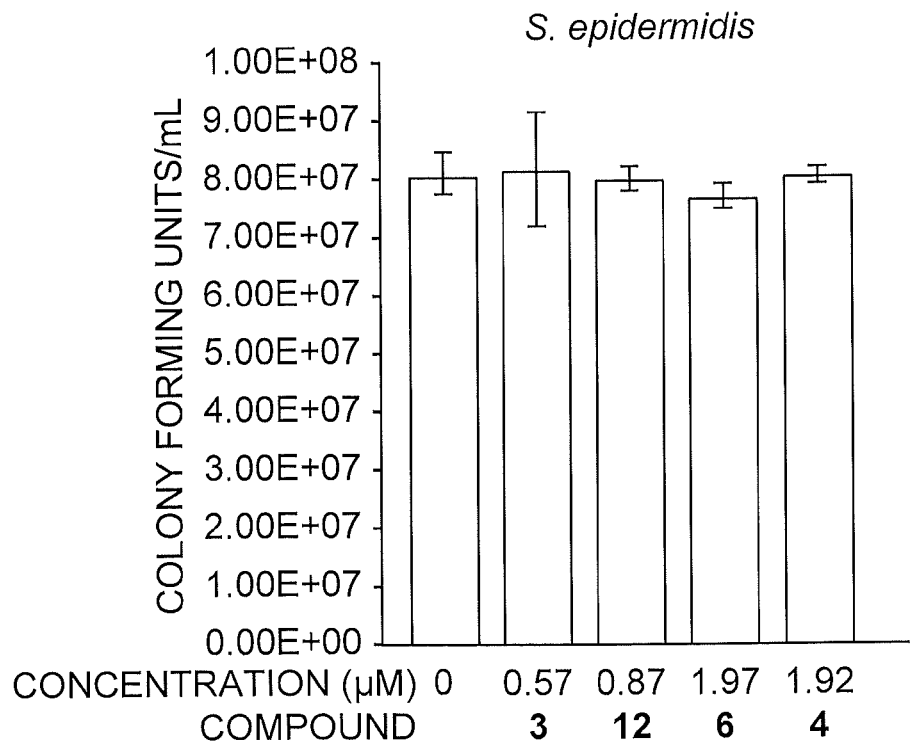
Figure 9A:
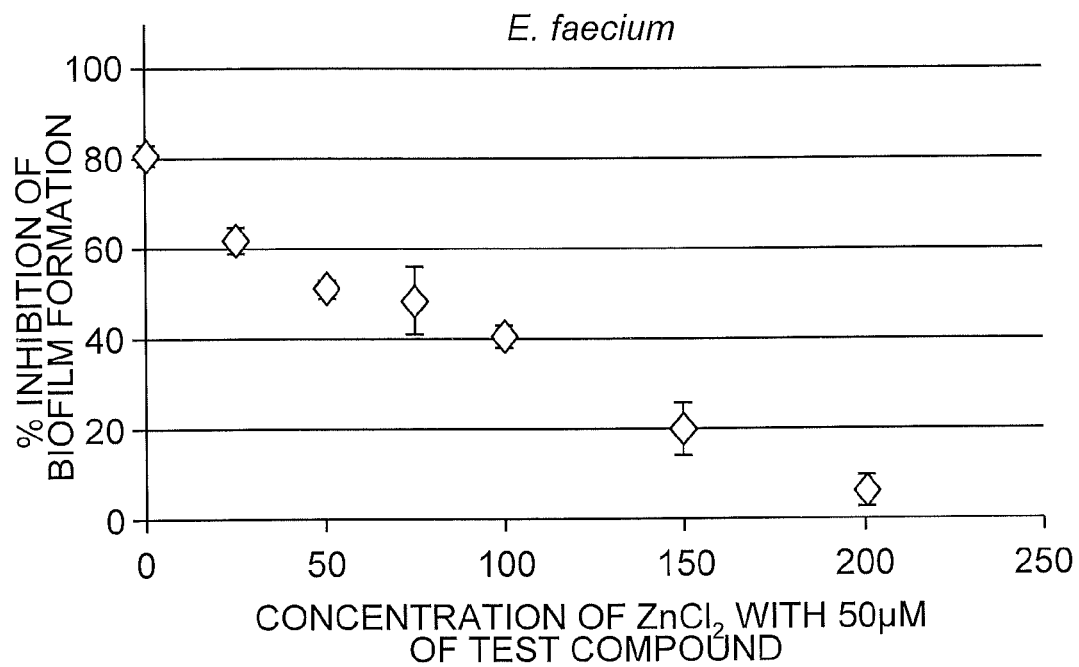
FIG. 9A-9B. Mitigating effects of zinc on *E. faecium*, MRSA and *S. epidermidis* biofilm formation inhibition induced by 2-(2-amino-1H-benzo[d]imidazol-6-ylcarbamoyl)-3,4,5,6-tetrachlorobenzoic acid hydrochloride. Biofilm inhibition was quantitated by measuring the $OD_{540}$ of each well in which a negative control lane wherein no biofilm was formed served as a background and was subtracted out. 200.0 μM $ZnCl_2$ was found to have no effect on biofilm formation. However, $ZnCl_2$ was found to mitigate the biofilm inhibition response induced by 2-(2-amino-1H-benzo[d]imidazol-6-yl-carbamoyl)-3,4,5,6-tetrachlorobenzoic acid hydrochloride in a dose response manner.
Figure 9B:
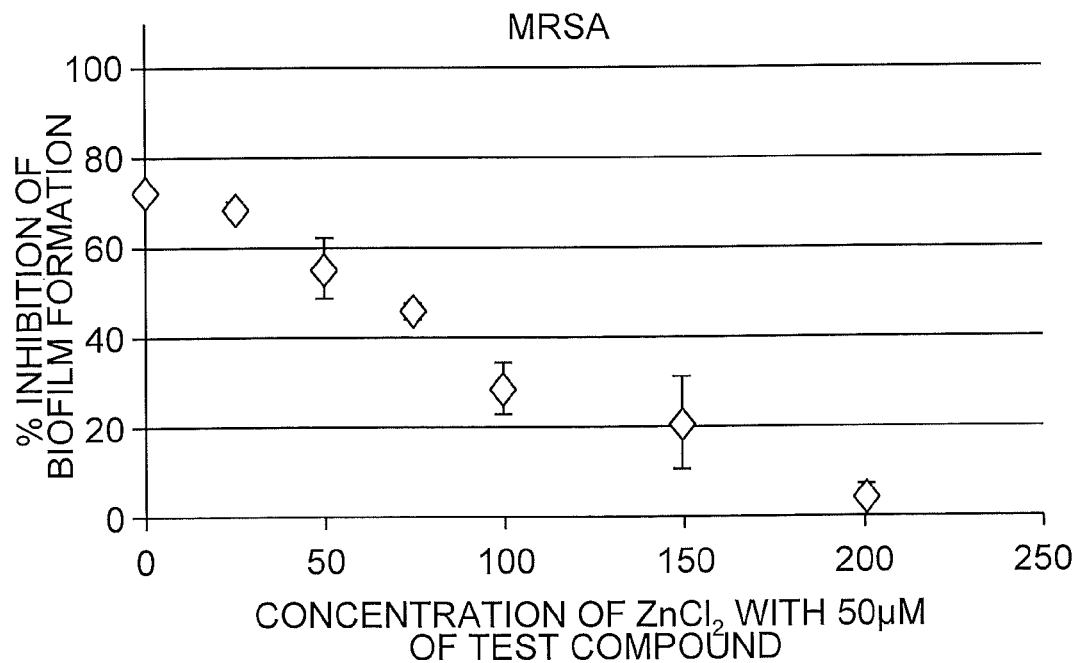

The present invention is further described below. All patent references referred to in this patent application are hereby incorporated by reference in their entirety as if set forth fully herein.

A. DEFINITIONS

"Benzimidazole" refers to the commonly known structure:

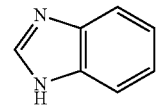

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom. "I" refers to an iodine atom. "F" refers to a fluorine atom.

An "acyl group" is intended to mean a group —C(O)—R, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). In some embodiments the alkyl can be a lower alkyl. "Lower alkyl" refers to straight or branched chain alkyl having from 1 to 3, or from 1 to 5, or from 1 to 8 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. In some embodiments, alkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

The term "optionally substituted" indicates that the specified group is either unsubstituted, or substituted by one or more suitable substituents. A "substituent" that is "substituted" is an atom or group which takes the place of a hydrogen atom on the parent chain or cycle of an organic molecule, for example, H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. In some embodiments, alkenyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like. In some embodiments, alkynyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. In some embodiments, cycloalkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Heterocyclo," as used herein, refers to a monocyclic, bicyclic or tricyclic ring system. Monocyclic heterocycle ring systems are exemplified by any 5 or 6 member ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. In some embodiments, heterocyclo groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Aryl" as used herein refers to a ring system having one or more aromatic rings. Representative examples of aryl include, azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl). In some embodiments, aryl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O. In some embodiments, heteroaryl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like. In some embodiments, alkoxy groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

An "amine" or "amino" is intended to mean the group —NH$_2$. "Optionally substituted" amines refers to —NH$_2$ groups wherein none, one or two of the hydrogens is replaced by a suitable substituent as described herein, such as alkyl, alkenyl, alkynyl, cycloalkyl, heterocyclo, aryl, heteroaryl, alkoxy, carbonyl, carboxy, etc. In some embodiments, one or two of the hydrogens are optionally substituted with independently selected, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide. Disubstituted amines may have substituents that are bridging, i.e., form a heterocyclic ring structure that includes the amine nitrogen.

An "amide" as used herein refers to an organic functional group having a carbonyl group (C=O) linked to a nitrogen atom (N), or a compound that contains this group, generally depicted as:

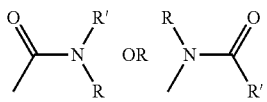

wherein, R and R' can independently be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "thiol" or "mercapto" refers to an —SH group or to its tautomer =S.

A "sulfone" as used herein refers to a sulfonyl functional group, generally depicted as:

wherein, R can be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "sulfoxide" as used herein refers to a sulfinyl functional group, generally depicted as:

wherein, R can be any covalently-linked atom or atoms, for example, H, halohydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "oxo," as used herein, refers to a =O moiety. The term "oxy," as used herein, refers to a —O— moiety.

"Nitro" refers to the organic compound functional group —NO$_2$.

"Carbonyl" is a functional group having a carbon atom double-bonded to an oxygen atom (—C=O). "Carboxy" as used herein refers to a —COOH functional group, also written as —CO$_2$H or —(C=O)—OH.

"Amino acid sidechain" as used herein refers to any of the 20 commonly known groups associated with naturally-occurring amino acids, or any natural or synthetic homologue thereof. An "amino acid" includes the sidechain group and the amino group, alpha-carbon atom, and carboxy groups, as commonly described in the art. Examples of amino acids include glycine, and glycine that is substituted with a suitable substituent as described herein, such as alkyl, alkenyl, alkynyl, cycloalkyl, heterocyclo, aryl, heteroaryl, alkoxy, carbonyl, carboxy, etc., or a pharmaceutically acceptable salt or prodrug thereof. For example, "Histidine" is one of the 20 most commonly known amino acids found naturally in proteins. It contains an imidazole side chain substituent. Other examples of naturally-occurring amino acids include lysine, arginine, aspartic acid, glutamic acid, asparagine, glutamine, serine, threonine, tyrosine, alanine, valine, leucine, isoleucine, phenylalanine, methionine, cryptophan, and cysteine. Also included in the definitions of "amino acid sidechain" and "amino acid" is proline, which is commonly included in the definition of an amino acid, but is technically an imino acid. As used in this application, both the naturally-occurring L-, and the non-natural D-amino acid enantiomers are included. The single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr). A "peptide" is a linear chain of amino acids covalently linked together, typically through an amide linkage, and contains from 1 or 2 to 10 or 20 or more amino acids, and is also optionally substituted and/or branched.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfates, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entirety.

"Form a ring" as used herein with respect to two substituents, e.g., $R^7$ and $R^8$ together forming a ring, refers to the two groups being linked together via one or more atoms (e.g., carbon) to form ring atoms making up a cycloalkyl, heterocyclo, aryl or heteroaryl as described herein. Rings may be part of a monocyclic, bicyclic or tricyclic moiety, each of such ring being a saturated or unsaturated member of the monocyclic, bicyclic or tricyclic moiety.

B. ACTIVE COMPOUNDS

Active compounds are provided below. In some of the embodiments provided in the present invention, active compounds are derivatives of benzimidazole. In some embodiments, active compounds include derivatives of 2-aminobenzimidazole (2-ABI). Active compounds as described herein can be prepared as detailed below or in accordance with known procedures or variations thereof that will be apparent to those skilled in the art.

As will be appreciated by those of skill in the art, the active compounds of the various formulas disclosed herein may contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present invention unless otherwise specified. Also included in active compounds of the invention are tautomers (e.g., tautomers of triazole and/or imidazole) and rotamers. All chains defined by the formulas herein which include three or more carbons may be saturated or unsaturated unless otherwise indicated.

Active compounds include compounds of Formula (I):

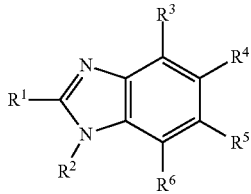

(I)

wherein:
$R^1$, $R^2$, $R^3$, $R^4$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (I), $R^1$ is a substituted amino, generally depicted by Formula (I)(a):

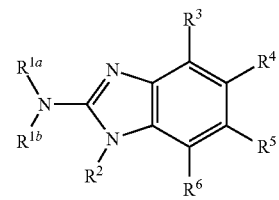

(I)(a)

wherein:
$R^{1a}$, $R^{1b}$, $R^2$, $R^3$, $R^4$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;
or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (I)(a), $R^{1a}$ and $R^{1b}$ are each H, generally depicted by Formula (I)(a)(i):

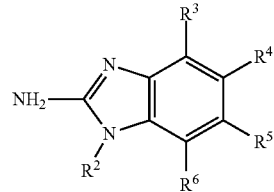

(I)(a)(i)

wherein:

R², R³, R⁴, R⁵ and R⁶ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, R², R³, R⁵ and R⁶ are each independently H or alkyl (e.g., lower alkyl having from 1 to 5 or from 1 to 10 carbon atoms).

In some embodiments, the substituent at R⁴ is substituted at least once with a halo and/or a carbonyl.

Active compounds also include compounds of Formula (II):

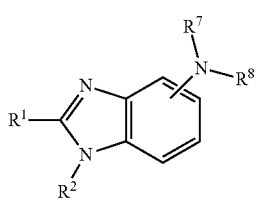

(II)

wherein:

R¹ and R² are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and R⁷ and R⁸ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein R⁷ and R⁸ together form a ring;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II), R¹ is a substituted amino, generally depicted by Formula (II)(a):

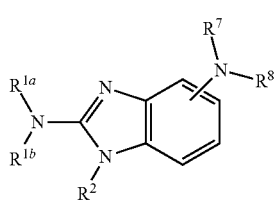

(II)(a)

wherein:

R¹ᵃ, R¹ᵇ and R² are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and R⁷ and R⁸ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein R⁷ and R⁸ together form a ring;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, R¹ᵃ, R¹ᵇ and R² are each independently H or alkyl (e.g., lower alkyl having from 1 to 5 or from 1 to 10 carbon atoms).

In some embodiments of Formula (II)(a), R¹ᵃ and R¹ᵇ are each H, generally depicted by Formula (II)(a)(i):

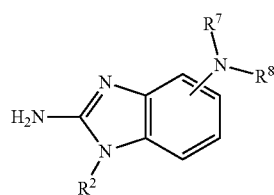

(II)(a)(i)

wherein:

R² is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and R⁷ and R⁸ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein R⁷ and R⁸ together form a ring;

or a pharmaceutically acceptable salt or prodrug thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, R² is H or alkyl (e.g., lower alkyl having from 1 to 5 or from 1 to 10 carbon atoms).

In some embodiments of Formula (II)(a)(i), R⁷ is acyl, generally depicted by Formula (II)(a)(i)(A):

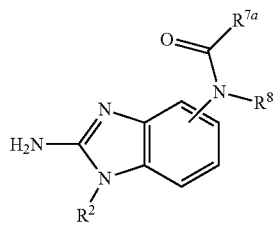

(II)(a)(i)(A)

wherein:

$R^2$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and $R^{7a}$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein $R^{7a}$ and $R^8$ together form a ring;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloallyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, $R^2$ is H or alkyl (e.g., lower alkyl having from 1 to 5 or from 1 to 10 carbon atoms). In some embodiments, $R^8$ is H or alkyl (e.g., lower alkyl having from 1 to 5 or from 1 to 10 carbon atoms).

In some embodiments, $R^{7a}$ is alkyl, alkenyl, alkynyl. In some embodiments, $R^{7a}$ is aryl. In some embodiments, the group at $R^{7a}$ has a carboxy substitution.

Examples of compounds of Formula (II)(a)(i)(A) include, but are not limited to, the following formulas:

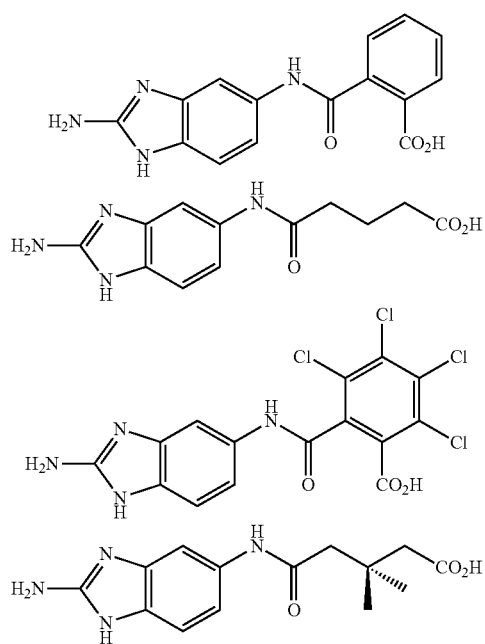

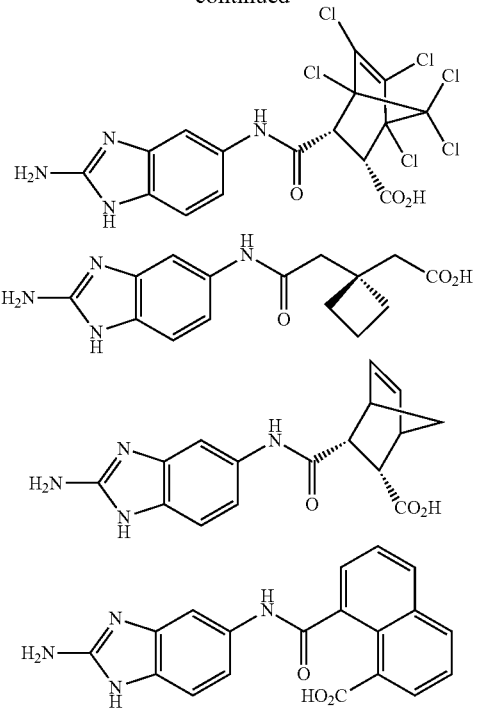

In some embodiments of Formula (II)(a)(i), $R^7$ and $R^8$ are each acyl, generally depicted by Formula (II)(a)(i)(B):

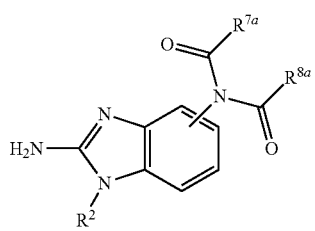

(II)(a)(i)(B)

wherein:

$R^2$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and $R^{7a}$ and $R^{8a}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein $R^{7a}$ and $R^{8a}$ together form a ring;

or a pharmaceutically acceptable salt or prodrug thereof. This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, $R^2$ is H or alkyl (e.g., lower alkyl having from 1 to 5 or from 1 to 10 carbon atoms).

Examples of compounds of Formula (II)(a)(i)(B) in which $R^2$ is H and $R^7$ and $R^{8a}$ together form a ring include, but are not limited to, the following formulas:

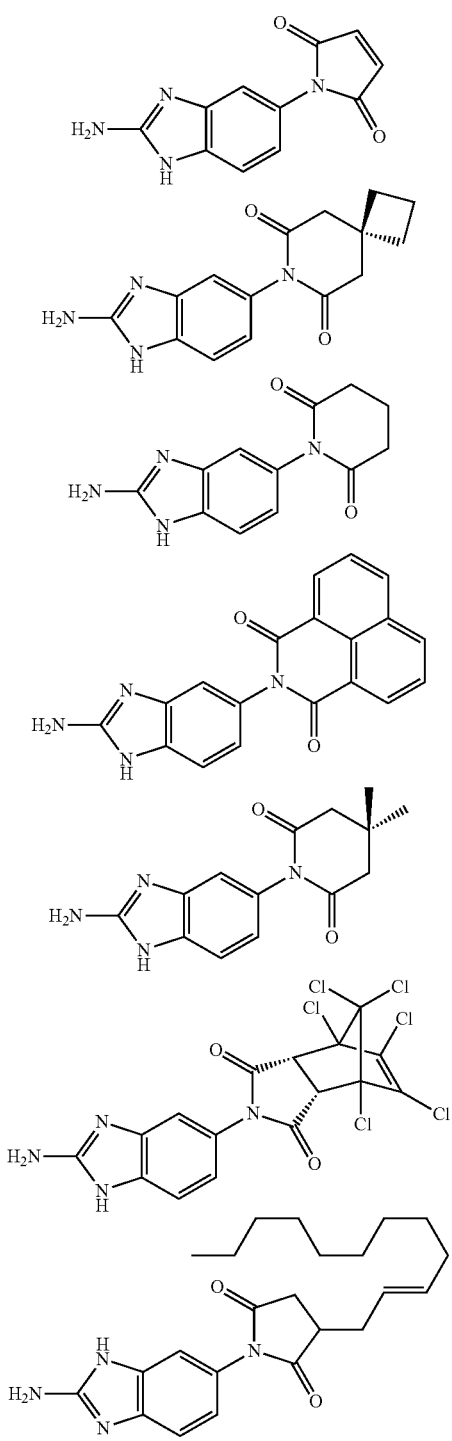

C. COMPOSITIONS

In some embodiments, biofilm preventing, removing or inhibiting compositions are provided, comprising a carrier and an effective amount of active compound. "Biofilm" or "biofilms" refer to communities of microorganisms that are attached to a substrate. The microorganisms often excrete a protective and adhesive matrix of polymeric compounds. They often have structural heterogeneity, genetic diversity, and complex community interactions. "Biofilm preventing", "biofilm removing", "biofilm inhibiting", "biofilm reducing", "biofilm resistant", "biofilm controlling" or "antifouling" refer to prevention of biofilm formation, inhibition of the establishment or growth of a biofilm, or decrease in the amount of organisms that attach and/or grow upon a substrate, up to and including the complete removal of the biofilm. As used herein, a "substrate" can include any living or nonliving structure. For example, biofilms often grow on synthetic materials submerged in an aqueous solution or exposed to humid air, but they also can form as floating mats on a liquid surface, in which case the microorganisms are adhering to each other or to the adhesive matrix characteristic of a biofilm.

"Dispersion" of a biofilm refers to the decrease in the amount of preformed biofilm, or decrease in the amount of organisms attached to a substrate, e.g., prior to administration of an active compound as described herein.

An "effective amount" of a biofilm preventing, removing or inhibiting composition is that amount which is necessary to carry out the composition's function of preventing, removing or inhibiting a biofilm. Similarly, an "effective amount" of a biofilm dispersion composition is that amount which is necessary to carry out the composition's function of dispersing a pre-formed biofilm.

In some embodiments, the carrier is a pharmaceutically acceptable carrier. A "pharmaceutically acceptable carrier" as used herein refers to a carrier that, when combined with an active compound of the present invention, facilitates the application or administration of that active compound for its intended purpose to prevent or inhibit biofilm formation, or remove an existing biofilm. The active compounds may be formulated for administration in a pharmaceutically acceptable carrier in accordance with known techniques. See, e.g., *Remington, The Science And Practice of Pharmacy* ($9^{th}$ Ed. 1995). The pharmaceutically acceptable carrier must, of course, also be acceptable in the sense of being compatible with any other ingredients in the composition. The carrier may be a solid or a liquid, or both, and is preferably formulated with the compound as a unit-dose composition, for example, a tablet, which may contain from 0.01 or 0.5% to 95% or 99% by weight of the active compound. One or more active compounds may be included in the compositions of the invention, which may be prepared by any of the well-known techniques of pharmacy comprising admixing the components, optionally including one or more accessory ingredients.

In general, compositions may be prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The compositions of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound that is being used. Preferred routes of parenteral administration include intrathecal injection and intraventricular injection into a ventricle of the brain.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one aspect of the present invention, there is provided an injectable, stable, sterile composition comprising an active compound as described herein, or a salt or prodrug thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by mixing the active compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers that may be used include petroleum jelly, lanoline, polyethylene glycols, alcohols, transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6):318 (1986)) and typically take the form of an optionally buffered aqueous solution of the active compound.

Also provided in some embodiments are compositions comprising an active compound and a biocide. A "biocide" as used herein refers to a substance with the ability to kill or to inhibit the growth of microorganisms (e.g., bacteria, fungal cells, protozoa, etc.), which substance is not an active compound give above in Section B. Common biocides include oxidizing and non-oxidizing chemicals. Examples of oxidizing biocides include chlorine, chlorine dioxide, and ozone. Examples of non-oxidizing biocides include quaternary ammonium compounds, formaldehyde, and anionic and non-anionic surface agents. Chlorine is the most common biocide used in sanitizing water systems.

An "antibiotic" as used herein is a type of "biocide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria such as *Escherichia coli* and *Klebsiella*, particularly *Pseudomonas aeroginosa*. Examples of aminoglycosides include, but are not limited to amikacin, gentamicin, kanamycin, neomycin, netilmicin, streptomycin, tobramycin, and paromomycin.

Carbapenems are broad-spectrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, meticillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), tinidazole, etc.

In some embodiments, a dentifrice composition is provided comprising the active compounds. A "dentifrice" is a substance that is used to clean the teeth. It may be in the form of, e.g., a paste or powder. Commonly known dentifrices include toothpaste, mouthwash, chewing gum, dental floss, and dental cream. Other examples of dentifrices include toothpowder, mouth detergent, troches, dental or gingival massage cream, dental strips, dental gels, and gargle tablets. Examples of dentifrice compositions comprising toothpaste and mouthwash are found in U.S. Pat. No. 6,861,048 (Yu et al.); U.S. Pat. No. 6,231,836 (Takhtalian et al.); and U.S. Pat. No. 6,331,291 (Glace et al.); each incorporated by reference herein in their entirety.

A coating composition is also provided. A "coating" as used herein is generally known. Any of a variety of organic and aqueous coating compositions, with or without pigments, may be modified to contain biofilm inhibiting compositions as described herein, including but not limited to those described in U.S. Pat. Nos. 7,109,262, 6,964,989, 6,835,459, 6,677,035, 6,528,580, 6,235,812, etc., each incorporated by reference herein in their entirety.

In general, the coatings comprise a film-forming resin, an aqueous or organic solvent that disperses the resin; and, optionally, at least one pigment. Other ingredients such as colorants, secondary pigments, stabilizers and the like can be included if desired. However, for use in the present invention the compositions further comprise one or more biofilm inhibiting compounds as described herein, which may be carried by or dispersed in the solvent and/or resin, so that the biofilm inhibiting compounds are dispersed or distributed on the substrate an article coated. A resin may carry the biofilm inhibiting compounds through covalent attachment through means well known in the art. The resin may comprise, for example, a polymeric material. A polymeric material is a material that is comprised of large molecules made from associated smaller repeating structural units, often covalently linked. Common examples of polymeric materials are unsaturated polyester resins, and epoxy resins.

Any suitable article can be coated, in whole or in part, with a composition of the invention. Suitable articles include, but are not limited to, automobiles and airplanes (including substrates such as wing and propeller surfaces for aerodynamic testing), vessel hulls (including interior and exterior surfaces thereof), pressure vessels (including interior and exterior surfaces thereof) medical implants, windmills, etc. Coating of the article with the composition can be carried out by any suitable means, such as by brushing, spraying, electrostatic deposition, dip coating, doctor blading, etc.

D. METHODS OF USE

Methods of controlling biofilm formation on a substrate are disclosed, comprising the step of administering an active compound to a substrate in an amount effective to inhibit biofilm formation. A "substrate" as used herein is a base on which an organism, such as those commonly found in biofilms, may live. The term "substrate," as used herein, refers to any substrate, whether in an industrial or a medical setting, that provides or can provide an interface between an object and a fluid, permitting at least intermittent contact between the object and the fluid. A substrate, as understood herein, further provides a plane whose mechanical structure, without further treatment, is compatible with the adherence of microorganisms. Substrates compatible with biofilm formation may be natural or synthetic, and may be smooth or irregular. Fluids contacting the substrates can be stagnant or flowing, and can flow intermittently or continuously, with laminar or turbulent or mixed flows. A substrate upon which a biofilm forms can be dry at times with sporadic fluid contact, or can have any degree of fluid exposure including total immersion. Fluid contact with the substrate can take place via aerosols or other means for air-borne fluid transmission.

Biofilm formation with health implications can involve those substrates in all health-related environments, including substrates found in medical environments and those substrates in industrial or residential environments that are involved in those functions essential to human well being, for example, nutrition, sanitation and the prevention of disease. Substrates found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Substrates found in the medical environment also include the inner and outer aspects of pieces of medical equipment, medical gear worn or carried by personnel in the health care setting. Such substrates can include counter tops and fixtures in areas used for medical procedures or for preparing medical apparatus, tubes and canisters used in respiratory treatments, including the administration of oxygen, of solubilized drugs in nebulizers and of anesthetic agents. Also included are those substrates intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such substrates can include handles and cables for medical or dental equipment not intended to be sterile. Additionally, such substrates can include those non-sterile external substrates of tubes and other apparatus found in areas where blood or body fluids or other hazardous biomaterials are commonly encountered.

Substrates in contact with liquids are particularly prone to biofilm formation. As an example, those reservoirs and tubes used for delivering humidified oxygen to patients can bear biofilms inhabited by infectious agents. Dental unit waterlines similarly can bear biofilms on their substrates, providing a reservoir for continuing contamination of the system of flowing an aerosolized water used in dentistry. Sprays, aerosols and nebulizers are highly effective in disseminating biofilm fragments to a potential host or to another environmental site. It is especially important to health to prevent biofilm formation on those substrates from where biofilm fragments can be carried away by sprays, aerosols or nebulizers contacting the substrate.

Other substrates related to health include the inner and outer aspects of those articles involved in water purification, water storage and water delivery, and articles involved in food processing. Substrates related to health can also include the inner and outer aspects of those household articles involved in providing for nutrition, sanitation or disease prevention. Examples can include food processing equipment for home use, materials for infant care, tampons and toilet bowls. "Substrate" as used herein also refers to a living substrate, such as the inner ear of a patent.

Substrates can be smooth or porous, soft or hard. Substrates can include a drainpipe, glaze ceramic, porcelain, glass, metal, wood, chrome, plastic, vinyl, Formica® brand laminate, or any other material that may regularly come in contact with an aqueous solution in which biofilms may form and grow. The substrate can be a substrate commonly found on household items such as shower curtains or liners, upholstery, laundry, and carpeting.

A substrate on which biofilm preventing, removing or inhibiting is important is that of a ship hull. Biofilms, such as those of *Halomonas pacifica*, promote the corrosion of the hull of ships and also increase the roughness of the hull, increasing the drag on the ship and thereby increasing fuel costs. The biofilm can also promote the attachment of larger living structures such as barnacles on the ship hull. Fuel can account for half of the cost of marine shipping, and the loss in fuel efficiency due to biofilm formation is substantial.

Substrates on which biofilms can adhere include those of living organisms, as in the case of humans with chronic infections caused by biofilms, as discussed above. Biofilms can also form on the substrates of food contact surfaces, such as those used for processing seafood, and also on food products themselves. Examples of seafood products that may have biofilm contamination include oysters. Human infections caused by the ingestion of raw oysters has been linked to *Vibrio vulnificus* bacterium. *Vibrio* bacteria attach to algae and plankton in the water and transfer to the oysters and fish that feed on these organisms.

Other examples of substrates or devices on which biofilms can adhere can be found in U.S. Pat. Nos. 5,814,668 and 7,087,661; and U.S. Pat. Appln. Publication Nos. 2006/0228384 and 2006/0018945, each of which is incorporated herein by reference in its entirety.

In some embodiments, methods of enhancing the effects of a biocide are disclosed, comprising the step of administering an active compound in combination with a biocide, the active compound being administered in an amount effective to enhance the effects of the biocide.

"Administering" or "administration of" an active compound and/or biocide as used herein in inclusive of contacting, applying, etc. (e.g., contacting with an aqueous solution, contacting with a surface (e.g., a hospital surface such as a table, instrumentation, etc.)), in addition to providing to a subject (for example, to a human subject in need of treatment for a microbial infection).

"Enhancing" the effects of a biocide by administering an active compound in combination with the biocide refers to increasing the effectiveness of the biocide, such that the microorganism killing and/or growth inhibition is higher at a certain concentration of the biocide administered in combination with the active compound than without. In some embodiments, a bacteria or other microorganism is "sensitized" to the effects of a biocide, such that the bacteria or other microorganism that was resistant to the biocide prior to administering the active compound (e.g., little to none, or less than 20, 10, 5 or 1% are killed upon application) is rendered vulnerable to that biocide upon or after administering the active compound (e.g., greater than 20, 30, 40, 50, 60, 70, 80, 90, or 95% or more are killed).

As used herein, the administration of two or more compounds (inclusive of active compounds and biocides) "in combination" means that the two compounds are administered closely enough in time that the administration of or presence of one alters the biological effects of the other. The two compounds may be administered simultaneously (concurrently) or sequentially.

Simultaneous administration of the compounds may be carried out by mixing the compounds prior to administration, or by administering the compounds at the same point in time but at different anatomic sites or using different routes of administration, or administered at times sufficiently close that the results observed are indistinguishable from those achieved when the compounds are administered at the same point in time.

Sequential administration of the compounds may be carried out by administering, e.g., an active compound at some point in time prior to administration of a biocide, such that the prior administration of active compound enhances the effects of the biocide (e.g., percentage of microorganisms killed and/or slowing the growth of microorganisms). In some embodiments, an active compound is administered at some point in time prior to the initial administration of a biocide. Alternatively, the biocide may be administered at some point in time prior to the administration of an active compound, and optionally, administered again at some point in time after the administration of an active compound.

Also disclosed is a method of controlling biofilm formation wherein the biofilm comprises Gram-negative or Gram-positive bacteria.

"Gram-negative" bacteria are those that do not retain crystal violet dye after an alcohol wash in the Gram staining protocol, while "Gram-positive" bacteria are those that are stained dark blue or violet color after an alcohol wash in the Gram staining protocol. This is due to structural properties in the cell walls of the bacteria. Gram-positive bacterial retain the crystal violet color due to a high amount of peptidoglycan in the cell wall.

Many genera and species of Gram-negative and Gram-positive bacteria are pathogenic. A "genus" is a category of biological classification ranking between the family and the species, comprising structurally or phylogenetically related species, or an isolated species exhibiting unusual differentiation. It is usually designated by a Latin or latinized capitalized singular noun. Examples of genera of biofilm-forming bacteria affected by active compounds of this invention include, but are not limited to, *Pseudomonas, Bordetella, Vibrio, Haemophilus, Halomonas*, and *Acinetobacter*.

"Species" refer to a category of biological classification ranking below the genus, and comprise members that are structurally or phylogenetically related, or an isolated member exhibiting unusual differentiation. Species are commonly designated by a two-part name, which name includes the capitalized and italicized name of the genus in which the species belongs as the first word in the name, followed by the second word that more specifically identifies the member of the genus, which is not capitalized. Examples of species of bacteria capable of forming biofilms that are affected by active compounds of the present invention include *Pseudomonas aeuroginosa, Bordetella bronchiseptica, Bordetella pertussis, Staphylococcus aureus, Vibrio vulnificus, Haemophilus influenzae, Halomonas pacifica*, and *Acinetobacter baumannii*.

Gram-negative bacteria include members of the phylum proteobacteria, which include genus members *Escherichia, Salmonella, Vibrio*, and *Helicobacter*.

Other examples of Gram-negative bacteria include, but are not limited to, bacteria of the genera *Klebsiella, Proteus, Neisseria, Helicobacter, Brucella, Legionella, Campylo-*

*bacter, Francisella, Pasteurella, Yersinia, Bartonella, Bacteroides, Streptobacillus, Spirillum, Moraxella* and *Shigella*.

Examples of Gram-positive bacteria include, but are not limited to, bacteria of the genera *Listeria, Staphylococcus, Streptococcus, Bacillus, Corynebacterium, Enterococcus, Peptostreptococcus*, and *Clostridium*. Examples include, but are not limited to, *Listeria monocytogenes, Staphylococcus aureus* (including methicillin-resistant *S. aureus*, or MSRA), *Staphylococcus epidermidis, Streptococcus pyogenes, Streptococcus pneumoniae, Bacillus cereus, Bacillus anthracia, Clostridium botulinum, Clostridium perfringens, Clostridium difficile, Clostridium tetani, Corynebacterium diphtheriae, Corynebacterium ulcerans, Enterococcus faecium* (including vancomycin-resistant *E. faecium*, or VRE), and *Peptostreptococcus anaerobius*.

Active compounds according to some embodiments bind, or are capable of binding, zinc(II). While not wishing to be bound by theory, the binding of zinc(II) by active compounds according to some embodiments may contribute to their activity in controlling biofilms of Gram-positive bacteria. Zinc(II) has been implicated in biofilm formation in Gram-positive species having G5 domains (Conrady et al., "A zinc-dependent adhesion module is responsible for intercellular adhesion in staphylococcal biofilms," Proc. Nat. Acad. Sci. USA 105(49): 19456-19461 (2008)).

Additional bacteria genera in which compounds disclosed herein may be useful in controlling biofilms include, but are not limited to, *Actinomyces, Propionibacterium, Nocardia* and *Streptomyces*. *Actinomyces* is a Gram-positive genus that includes opportunistic pathogens in humans and animals, e.g., in the oral cavity, and can cause actinomycosis (cause by, e.g., *Actinomyces israelii*). *Propionibacterium acnes* is a Gram-positive species that can cause acne and chronic blepharitis and endophthalmitis (e.g., after intraocular surgury). *Nocardia* is a Gram-positive genus that includes opportunistic pathogenic species causing, e.g., slowly progressive pneumonia, encephalitis, etc. *Streptomyces* is a Gram-positive genus that occasionally are found in human infections, such as mycetoma (caused by, e.g., *S. somaliensis* and *S. sudanensis*).

A method for treating a chronic bacterial infection in a subject in need thereof is disclosed, comprising administering active compound to said subject in an amount effective to inhibit, reduce, or remove a biofilm component of said chronic bacterial infection. "Treating" as used herein refers to any type of activity that imparts a benefit to a patient afflicted with a disease, including improvement in the condition of the patient (e.g., in one or more symptoms), delay in the progression of the disease, delay in onset of the disease, etc. The present invention is primarily concerned with the treatment of human subjects, but the invention may also be carried out on animal subjects, particularly mammalian subjects (e.g., mice, rats, dogs, cats, rabbits, and horses), avian subjects (e.g., parrots, geese, quail, pheasant), livestock (e.g., pigs, sheep, goats, cows, chickens, turkey, duck, ostrich, emu), reptile and amphibian subjects, for veterinary purposes or animal husbandry, and for drug screening and drug development purposes.

A "chronic bacterial infection" is a bacterial infection that is of a long duration or frequent recurrence. For example, a chronic middle ear infection, or otitis media, can occur when the Eustachian tube becomes blocked repeatedly due to allergies, multiple infections, ear trauma, or swelling of the adenoids. The definition of "long duration" will depend upon the particular infection. For example, in the case of a chronic middle ear infection, it may last for weeks to months. Other known chronic bacterial infections include urinary tract infection (most commonly caused by *Escherichia coli* and/or *Staphylococcus saprophyticus*), gastritis (most commonly caused by *Helicobacter pylori*), respiratory infection (such as those commonly afflicting patents with cystic fibrosis, most commonly caused by *Pseudomonas aeuroginosa*), cystitis (most commonly caused by *Escherichia coli*), pyelonephritis (most commonly caused by Proteus species, *Escherichia coli* and/or *Pseudomonas* species), osteomyelitis (most commonly caused by *Staphylococcus aureus*, but also by *Escherichia coli*), bacteremia, skin infection, rosacea, acne, chronic wound infection, infectious kidney stones (can be caused by *Proteus mirabilis*), bacterial endocarditis, and sinus infection. A common infection afflicting pigs is atrophic rhinitis (caused by *Bordatella* species, e.g. *Bordatella bronchiseptica, Bordatella rhinitis*, etc.).

Various nosocomial infections that are especially prevalent in intensive care units implicate *Acinetobacter* species such as *Acinetobacter baumannii* and *Acinetobacter lwoffi*. *Acinetobacter baumanni* is a frequent cause of nosocomial pneumonia, and can also cause skin and wound infections and bacteremia. *Acinetobacter lwoffi* causes meningitis. The *Acinetobacter* species are resistant to many classes of antibiotics. The CDC has reported that bloodstream infections implicating *Acinetobacter baumanni* were becoming more prevalent among service members injured during the military action in Iraq and Afghanistan.

*Staphylococcus aureus* is a common cause of nosocomial infections, often causing post-surgical wound infections. *Staphylococcus aureus* can also cause variety of other infections in humans (e.g., skin infections), and can contribute to mastitis in dairy cows. *Staphylococcus aureus* has become resistant to many of the commonly used antibiotics.

Also disclosed is a method of clearing a preformed biofilm from a substrate comprising the step of administering an effective amount of compound to said substrate, wherein said effective amount will reduce the amount of said biofilm on said substrate. "Preformed biofilm" is a biofilm that has begun to adhere to a substrate. The biofilm may or may not yet be fully formed.

E. DEVICES

Medical devices comprising a substrate and an effective amount of active compound are also disclosed. "Medical device" as used herein refers to an object that is inserted or implanted in a subject or applied to a surface of a subject. Common examples of medical devices include stents, fasteners, ports, catheters, scaffolds and grafts. A "medical device substrate" can be made of a variety of biocompatible materials, including, but not limited to, metals, ceramics, polymers, gels, and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate, etc. Medical devices can also be fabricated using naturally-occurring materials or treated with naturally-occurring materials. Medical devices can include any combination of artificial materials, e.g., combinations selected because of the particular characteristics of the components. Medical devices can be intended for short-term or long-term residence where they are positioned. A hip implant is intended for several decades of use, for example. By contrast, a tissue expander may only be needed for a few months, and is removed thereafter.

Some examples of medical devices are found in U.S. Pat. No. 7,081,133 (Chinn et al.); U.S. Pat. No. 6,562,295 (Neuberger); and U.S. Pat. No. 6,387,363 (Gruskin); each incorporated by reference herein in its entirety.

F. COVALENT COUPLING OF ACTIVE COMPOUNDS

In some embodiments, active compounds as described herein are covalently coupled to substrates. Examples of substrates include solid supports and polymers. The polymers, typically organic polymers, may be in solid form, liquid form, dispersed or solubilized in a solvent (e.g., to form a coating composition as described above), etc. The solid support may include the substrate examples as described above to be coated with or treated with active compounds of the invention.

Covalent coupling can be carried out by any suitable technique. Active compounds of the present invention may be appended to a substrate via aldehyde condensation, amine bond, amide or peptide bond, carbon-carbon bond, or any suitable technique commonly used in the art. See also U.S. Patent Application Publication No. 2008/0181923 to Melander et al., which is incorporated by reference herein. A preferred method according to some embodiments is amine or amide bond formation. Further examples and explanations of these types of reactions can be found in U.S. Pat. No. 6,136,157 (Lindeberg et al.) and U.S. Pat. No. 7,115,653 (Baxter et al.), which are each hereby incorporated by reference in their entirety.

Various coupling reactions can be used to covalently link active compounds of the present invention to a substrate. Examples of coupling reactions that can be used include, but are not limited to, Hiyama, Suzuki, Sonogashira, Heck, Stille, Negishi, Kumada, Wurtz, Ullmann, Cadiot-Chodkiewicz, Buchwald-Hartwig, and Grignard reactions. For example, an active compound that is substituted with a halide (e.g. bromo or chloro) can be coupled to a substrate via a Heck reaction.

Some aspects of the present invention are described in more detail in the following non-limiting examples.

Example 1

The decision to study the 2-ABI scaffold was based upon previous studies in our group that analyzed the anti-biofilm properties of a number of small molecules based upon the natural product bromoageliferin (see Melander et al., U.S. Patent Application Publication 2008/0181923). One of the first derivatives studied was TAGE, a bicyclic 2-aminoimidazole (2-AI) that represented the core architecture of bromoageliferin. The 2-ABI scaffold is a readily accessible, aromatized analogue of TAGE, which we hypothesized would provide unique and/or improved anti-biofilm properties in comparison to these 2-AI derivatives.

A preliminary library of 2-ABI analogues was synthesized for anti-biofilm evaluation (Scheme 1). An isomeric mixture of tri-boc protected 5-amino, 2-ABI (1) (Kikuchi et al., Bioorg. Med. Chem. 14:6189-6196 (2006)) was acylated with an array of cyclic anhydrides that were subsequently deprotected to generate an initial set of 2-ABI derivatives. A related set of 2-ABI derivatives was also synthesized in which 1 was reacted with cyclic anhydrides under refluxing toluene, which, followed by boc-deprotection delivered to the target 2-ABI-imides.

Scheme 1. Synthesis of 2-aminobenzimidazole library

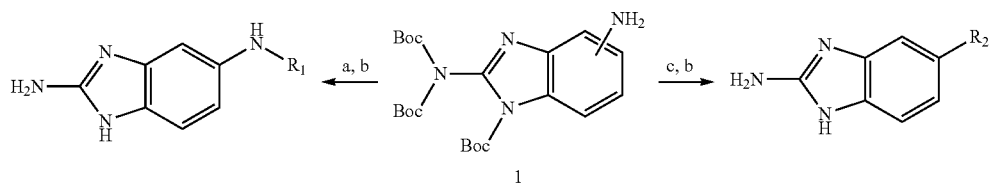

(reaction conditions: (a) cyclic anhydride, $CH_2Cl_2$; (b) HCl, $H_2O$, THF; (c) cyclic anhydride, Toluene, 110° C.).

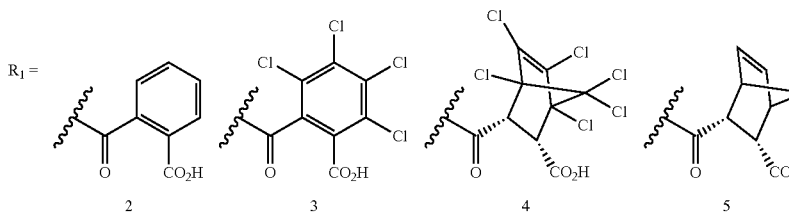

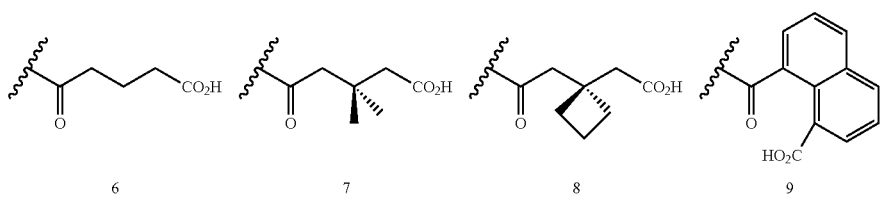

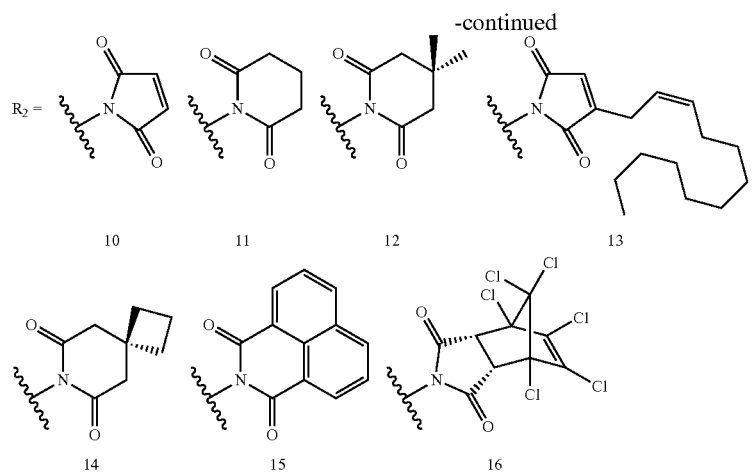

Each compound was screened at 100 μM for its ability to inhibit the formation of *Pseudomonas aeruginosa* PAO1 and multidrug resistant *Acinetobacter baumannii* (MDRAB) biofilms. As opposed to the 2-AI class of anti-biofilm agents, none of these 2-ABI derivatives was able to inhibit biofilm formation of either γ-proteobacteria at this concentration.

Next, each compound was screened for its ability to inhibit biofilm development in three Gram-positive bacterial strains that are prominent in human medicine. The three strains chosen where MRSA, vancomycin-resistant *Enterococcus faecium* (VRE), and *Staphylococcus epidermidis*. Again, all 2-ABI derivatives were initially screened at 100 μM. Each compound was able to inhibit biofilm development of at least two of the bacterial strains at this concentration.

A dose-response study was then initiated in which both the $IC_{50}$ and $EC_{50}$ value of each compound towards the bacterial strains were determined (Table 1). Here, $IC_{50}$ is defined as the concentration of compound that inhibits 50% biofilm development while $EC_{50}$ is defined as the concentration of compound that disperses 50% of a pre-formed biofilm. Of these compounds, 2-ABI derivative 3 had the best activity profile, with $IC_{50}/EC_{50}$ values of 860 nM/2.92 μM (MRSA), 1.40 μM/74.8 μM (VRE), and 570 nM/7.25 μM (*S. epidermidis*).

Growth curve and colony count analysis demonstrated that each compound was non-microbicidal.

Next the mechanistic basis of how compound 3 was able to inhibit and disperse bacterial biofilms was investigated. Iron levels are known to effect Gram-positive biofilm development (Deighton, M.; Borland, R. *Infection and Immunity* 1993, 61, 4473-4479) and were deemed a plausible driver of the observed anti-biofilm activity. To examine Fe(II) related antibiofilm behavior, a dose-dependent study was performed in which the ability of 3 to inhibit biofilm development was measured under increasing Fe(II) concentration. It was noted that the activity of 3 was not affected by increasing Fe(II) concentrations, indicating that iron homoeostasis was not involved in 2-ABI anti-biofilm activity.

Next, Zn(II) homeostasis was examined. Zn(II) has been implicated in the pathogenesis of Gram-positive bacterial infections and may be an important regulator of biofilm formation (Conrady, D. G.; Brescia, C. C.; Horii, K.; Weiss, A. A.; Hassett, D. J.; Herr, A. B. *Proceedings of the National Academy of Sciences of the United States of America* 2008, 105, 19456-19461). As opposed to the Fe(II) study, it was noted that Zn(II), in a dose-dependent manner, suppressed the ability of 3 to inhibit biofilm development in each Gram-positive bacteria. When supplemented with 200 μM $ZnCl_2$, 3 was unable to inhibit biofilm formation.

TABLE 1

| | Biofilm inhibition and dispersion data. | | |
|---|---|---|---|
| Compound | MRSA $IC_{50}$ \| $EC_{50}$ (μM) | VRE $IC_{50}$ \| $EC_{50}$ (μM) | *S. epidermidis* $IC_{50}$ \| $EC_{50}$ (μM) |
| 2 | 5.9 ± 1.3 \| 35 ± 2.8 | 21 ± 2.9 \| 75 ± 6.7 | 32 ± 3.8 \| 44 ± 7.9 |
| 3 | 0.89 ± 0.01 \| 2.9 ± 0.4 | 1.4 ± 0.4 \| 75 ± 2.1 | 0.57 ± 0.2 \| 7.3 ± 0.2 |
| 4 | 1.5 ± 0.4 \| 6.6 ± 0.2 | 210 ± 35 \| 280 ± 8.3 | 1.9 ± 0.4 \| 19 ± 5.8 |
| 5 | 16 ± 2.9 \| 63 ± 6.9 | 63 ± 9.1 \| 107 ± 11 | 4.1 ± 2.0 \| 45 ± 6.1 |
| 6 | >300 \| >300 | 22 ± 8.3 \| 88 ± 5.2 | 1.9 ± 0.9 \| 13 ± 6.1 |
| 7 | 69 ± 2.7 \| 205 ± 15 | 0.9 ± 0.3 \| 94 ± 10 | 240 ± 20 \| 260 ± 6.7 |
| 8 | 103 ± 6.3 \| 250 ± 19 | 2.4 ± 0.7 \| >300 | 73 ± 8.2 \| 175 ± 8.5 |
| 9 | >300 \| >300 | 0.9 ± 0.4 \| 6.3 ± 1.9 | 6.2 ± 1.2 \| 30 ± 5.7 |
| 10 | 2.8 ± 0.8 \| 36 ± 1.7 | 7.7 ± 0.8 \| 150 ± 8.4 | 180 ± 17 \| 266 ± 7.3 |
| 11 | 17 ± 1.9 \| 25 ± 2.0 | 1.6 ± 0.9 \| 280 ± 4.8 | 12 ± 1.0 \| 137 ± 15 |
| 12 | 48 ± 4 \| 101 ± 6 | 16 ± 4.7 \| 203 ± 5.5 | 0.9 ± 0.3 \| 17 ± 4.0 |
| 13 | 9.6 ± 0.8 \| 14 ± 2.9 | 6.9 ± 2.2 \| 30 ± 8.5 | 15 ± 2.7 \| 70 ± 4.2 |
| 14 | 42 ± 2.4 \| 48 ± 2.1 | 1.9 ± 0.5 \| 230 ± 9.6 | 170 ± 14 \| 180 ± 13 |
| 15 | >300 \| >300 | 69 ± 10 \| 110 ± 2.9 | 24 ± 6.3 \| 81 ± 4.9 |
| 16 | 5.7 ± 0.5 \| 9.5 ± 2.5 | 7.4 ± 1.7 \| 31 ± 7.8 | 1.5 ± 0.5 \| 33 ± 3.7 |

Given this Zn(II)-dependence, the ability of 3 to bind zinc directly was determined to ascertain if the mechanism was potentially occurring via a Zn(II)-binding mechanism. To answer this question, an $^1$H NMR binding experiment was performed in which the chemical shifts of 3 were measured in the presence of 0 equivalents, 0.5 equivalents, and 1.0 equivalents ZnCl$_2$. Comparison of the aromatic peaks clearly indicates peak broadening as ZnCl$_2$ is titrated in, indicating that 3 is directly binding ZnCl$_2$. As a control, the same experiment was performed with FeSO$_4$. No change in the NMR signal of 3 was observed with 0, 0.5, or 1.0 equivalents FeSO$_4$.

Finally, two control compounds were tested (17 and 18) to probe if substructures within 3 were responsible for the anti-biofilm activity.

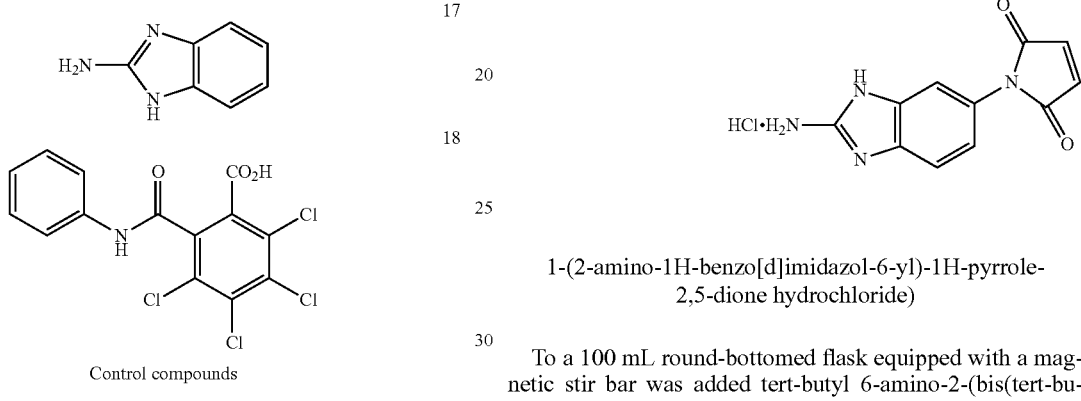

Control compounds

Neither compound was able to inhibit MRSA, VRE, or *S. epidermidis* biofilm formation at 100 μM (highest concentration tested). Furthermore, no change was noted in either $^1$H NMR spectrum in the absence or presence of ZnCl$_2$.

In conclusion, a novel inhibitor and disperser of Gram-positive biofilms based upon a 2-ABI scaffold has been identified that appears to operate via a Zn(II)-dependent mechanism. Preliminary NMR studies indicate that this compound binds zinc directly. These 2-ABI molecules are some of the most potent anti-biofilm agents identified to date that do not operate through a microbicidal mechanism.

Example 2

Protocols for 2-ABI Synthesis and Activity Testing

All reagents used for chemical synthesis were purchased from commercially available sources and used without further purification. Chromatography was performed using 60 Å mesh standard grade silica gel from Sorbtech. NMR solvents were obtained from Cambridge Isotope Labs and used as is. NMR (300 MHz or 400 MHz) and $^{13}$C NMR (75 MHz or 100 MHz) spectra were recorded at 25° C. on Varian Mercury spectrometers. Chemical shifts (δ) are given in ppm relative to tetramethylsilane or the respective NMR solvent; coupling constants (J) are in hertz (Hz). Abbreviations used are s=singlet, bs=broad singlet, d=doublet, dd=doublet of doublets, t=triplet, dt=doublet of triplets, bt=broad triplet, qt=quartet, m=multiplet, bm=broad multiplet and br=broad. Mass spectra were obtained at the NCSU Department of Chemistry Mass Spectrometry Facility.

MRSA (ATCC #BAA-44), *Enterococcus faecium* (ATCC #51559), MDRAB (ATCC #BAA-1605) and *Staphylococcus epidermidis* (ATCC #29886) were obtained from the ATCC. *P. aeruginosa* strain PAO1 was provided by Dr. Wozniak at Wake Forest School of Medicine. All other supplies were purchased from commercially available sources.

Synthesis

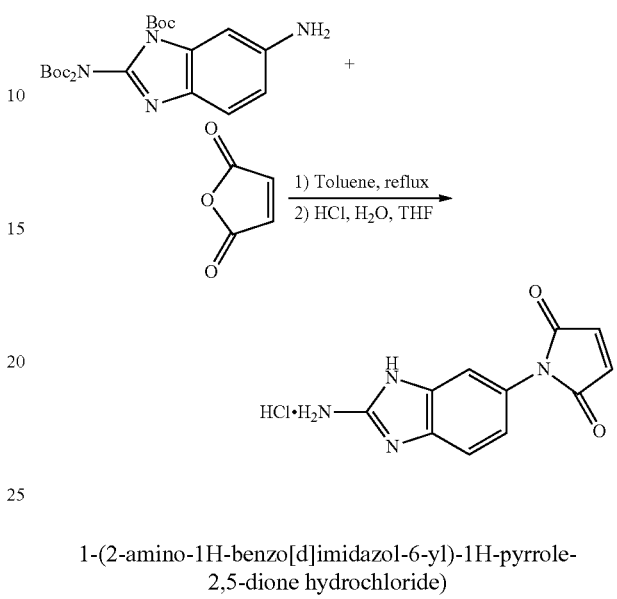

1-(2-amino-1H-benzo[d]imidazol-6-yl)-1H-pyrrole-2,5-dione hydrochloride)

To a 100 mL round-bottomed flask equipped with a magnetic stir bar was added tert-butyl 6-amino-2-(bis(tert-butoxycarbonyl)amino)-1H-benzo[d]imidazole-1-carboxylate (0.102 g, 0.227 mmol), toluene (20 mL) and maleic anhydride (0.022 g, 0.227 mmol). The stirring solution was allowed to warm to 120° C. and then to continue stirring for two hours. Volatiles were evaporated under reduced pressure. The resulting residue was dissolved up in a 1:1:2 mixture of concentrated HCl, H$_2$O and THF (10 mL) and allowed to stir for seven hours with ventilation. Volatiles were then evaporated under reduced pressure. The resulting solid was rinsed thoroughly with ether providing the title compound (0.052 g, 87% yield) as a yellow solid. $^1$H NMR (300 MHz, CD$_3$OD) δ 7.51 (s, 2H), δ 7.32 (d, 1H), δ 6.33 (s, 2H) ppm; $^{13}$C NMR (75 MHz, CD$_3$OD) δ 167.9, 130.6, 130.5, 126.5, 118.5, 118.5, 112.5, 106.8 ppm; HRMS (ESI) Calcd for C$_{11}$H$_8$N$_4$O$_2$ (M+) 228.0647, 228.0641.

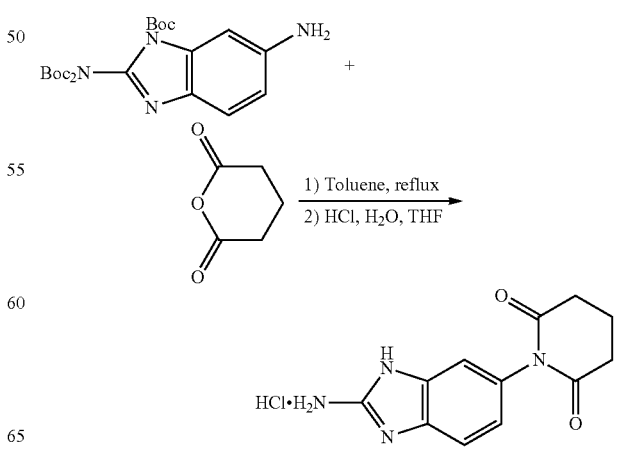

1-(2-amino-1H-benzo[d]imidazol-6-yl)piperidine-2,6-dione hydrochloride

Following the same procedure to synthesize 1-(2-amino-1H-benzo[d]imidazol-6-yl)-1H-pyrrole-2,5-dione hydrochloride, tert-butyl 6-amino-2-(bis(tert-butoxycarbonyl)amino)-1H-benzo[d]imidazole-1-carboxylate (0.113 g, 0.252 mmol) was reacted with glutaric anhydride (0.029 g, 0.252 mmol) to give the title compound (0.066 g, 93% yield) as a white solid. $^1$H NMR (300 MHz, CD$_3$OD) δ 7.85 (s, 1H), δ 7.28 (s, 2H), δ 2.42 (m, 4H), δ 1.97 (m, 2H) ppm; $^{13}$C NMR (75 MHz, CD$_3$OD) δ 174.1, 172.6, 135.2, 129.8, 125.9, 103.6, 35.6, 32.9, 20.9 ppm; HRMS (ESI) Calcd for C$_{12}$H$_{12}$N$_4$O$_2$ (M+) 244.0960. Found 244.0969.

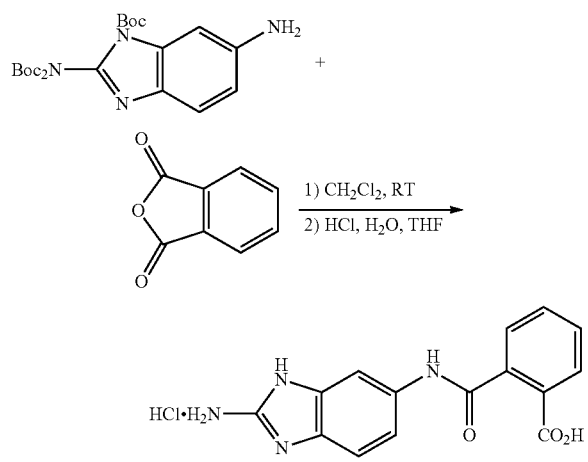

2-(2-amino-1H-benzo[d]imidazol-6-ylcarbamoyl)benzoic acid hydrochloride

To a 100 mL round-bottomed flask equipped with a magnetic stir bar was added tert-butyl 6-amino-2-(bis(tert-butoxycarbonyl)amino)-1H-benzo[d]imidazole-1-carboxylate (0.142 g, 0.317 mmol), dichoromethane (10 mL) and isobenzofuran-1,3-dione (0.047 g, 0.317 mmol). The stirring solution was allowed stir for 24 hours at room temperature. Volatiles were evaporated under reduced pressure. The resulting residue was dissolved up in a 1:1:2 mixture of concentrated HCl, H$_2$O and THF (10 mL) and allowed to stir for seven hours with ventilation. Volatiles were then evaporated under reduced pressure. The resulting solid was rinsed thoroughly with ether providing the title compound (0.083 g, 81% yield) as a yellow solid. $^1$H NMR (300 MHz, CD$_3$OD) δ 7.95 (d, 1H), δ 7.71 (m, 2H), δ 7.59 (m, 2H), δ 7.47 (m, 1H), δ 7.30 (t, 1H) ppm; $^{13}$C NMR (75 MHz, CD$_3$OD) δ 170.1, 132.9, 130.9, 130.2, 128.6, 126.5, 123.4, 118.2, 117.8, 112.1 ppm; HRMS (ESI) Calcd for C$_{15}$H$_{12}$N$_4$O$_2$ (M+) 296.0909. Found 296.0915.

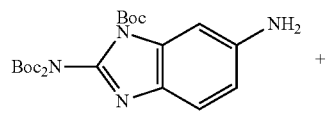

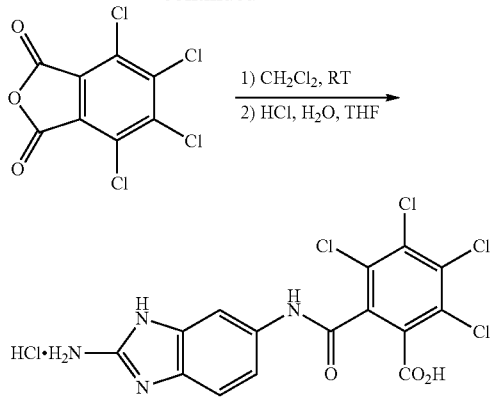

2-(2-amino-1H-benzo[d]imidazol-6-ylcarbamoyl)-3,4,5,6-tetrachlorobenzoic acid hydrochloride Following the same procedure to synthesize 2-(2-amino-1H-benzo[d]imidazol-6-ylcarbamoyl)benzoic acid hydrochloride, tert-butyl 6-amino-2-(bis(tert-butoxycarbonyl)amino)-1H-benzo[d]imidazole-1-carboxylate (0.100 g, 0.223 mmol) was reacted with 4,5,6,7-tetrachloroisobenzofuran-1,3-dione (0.064 g, 0.223 mmol) to give the title compound (0.081 g, 77% yield) as a yellow solid. $^1$H NMR (300 MHz, CD$_3$OD) δ 7.32 (s, 2H), δ 7.12 (s, 1H) ppm; $^{13}$C NMR (75 MHz, CD$_3$OD) δ 198.8, 165.5, 152.2, 134.7, 133.5, 130.6, 130.2, 129.6, 126.5, 118.5, 112.5, 106.7 ppm; HRMS (ESI) Calcd for C$_{15}$H$_8$Cl$_4$N$_4$O$_3$ (M+) 431.9351. Found 431.9359.

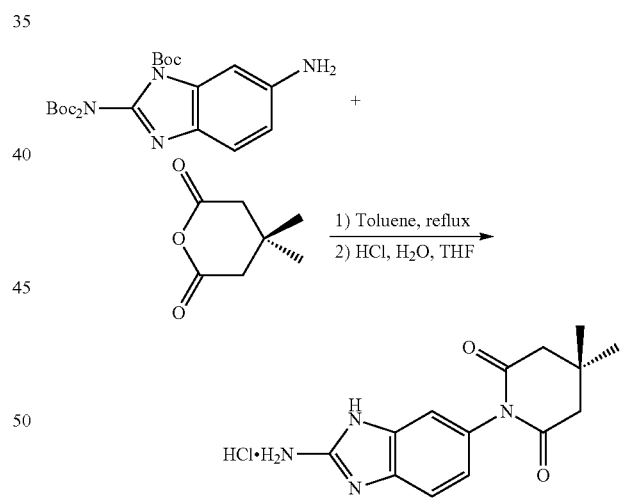

1-(2-amino-1H-benzo[d]imidazol-6-yl)-4,4-dimethylpiperidine-2,6-dione hydrochloride Following the same procedure to synthesize 1-(2-amino-1H-benzo[d]imidazol-6-yl)-1H-pyrrole-2,5-dione hydrochloride, tert-butyl 6-amino-2-(bis(tert-butoxycarbonyl)amino)-1H-benzo[d]imidazole-1-carboxylate (0.300 g, 0.669 mmol) was reacted with 4,4-dimethyldihydro-2H-pyran-2,6(3H)-dione (0.095 g, 0.669 mmol) to give the title product (0.202 g, 98% yield) as a yellow solid. $^1$H NMR (300 MHz, CD$_3$OD) δ 7.86 (s, 1H), δ 7.28 (s, 2H), δ 2.49 (s, 2H), δ 2.39 (s, 2H), δ 1.15 (s, 6H) ppm; $^{13}$C NMR (75 MHz, CD$_3$OD) 174.8, 171.7, 151.2, 134.9, 129.8, 126.1, 116.4, 111.3, 103.8, 45.4, 33.1, 27.2 ppm; HRMS (ESI) Calcd for C$_{14}$H$_{16}$N$_4$O$_2$ (M+) 272.1273. Found 272.1282.

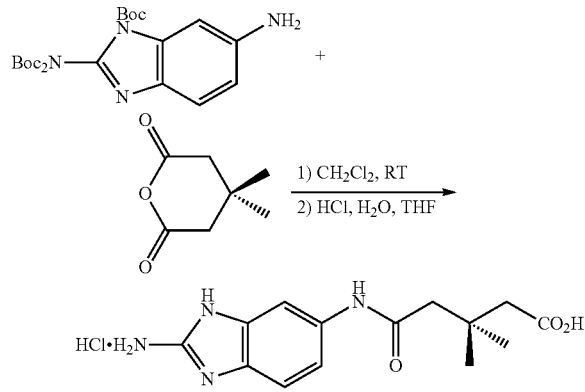

5-(2-amino-1H-benzo[d]imidazol-6-ylamino)-3,3-dimethyl-5-oxopentanoic acid hydrochloride Following the same procedure to synthesize 2-(2-amino-1H-benzo[d]imidazol-6-ylcarbamoyl)benzoic acid hydrochloride, tert-butyl 6-amino-2-(bis(tert-butoxycarbonyl)amino)-1H-benzo[d]imidazole-1-carboxylate (0.157 g, 0.351 mmol) was reacted with 4,4-dimethyldihydro-2H-pyran-2,6(3H)-dione (0.049 g, 0.351 mmol) to give the title product (0.107 g, 93% yield) as a yellow solid. $^1$H NMR (300 MHz, CD$_3$OD) δ 7.81 (s, 1H), δ 7.29 (m, 2H), δ 2.45 (m, 4H), 1.16 (m, 6H) ppm; $^{13}$C NMR (75 MHz, CD$_3$OD) 174.8, 173.6, 173.1, 171.9, 171.6, 151.2, 134.7, 129.6, 111.5, 103.9, 33.2, 33.1, 29.1, 27.3, 26.9 ppm; HRMS (ESI) Calcd for C$_{14}$H$_{19}$N$_4$O$_3$ (M+) 290.1378. Found 290.1380.

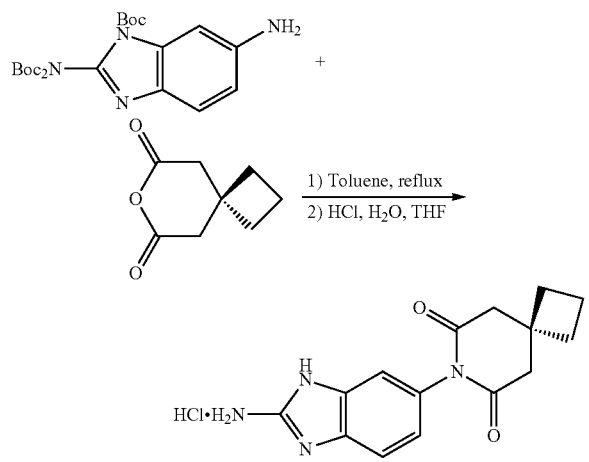

(S)-7-(2-amino-1H-benzo[d]imidazol-6-yl)-7-azaspiro[3.5]nonane-6,8-dione hydrochloride Following the same procedure to synthesize 1-(2-amino-1H-benzo[d]imidazol-6-yl)-1H-pyrrole-2,5-dione hydrochloride, tert-butyl 6-amino-2-(bis(tert-butoxycarbonyl)amino)-1H-benzo[d]imidazole-1-carboxylate (0.301 g, 0.671 mmol) was reacted with (S)-7-oxaspiro[3.5]nonane-6,8-dione (0.103 g, 0.671 mmol) to give the desired product (0.215 g, 78% yield) as a yellow solid. $^1$H NMR (300 MHz, CD$_3$OD) δ 7.83 (s, 1H), δ 7.27 (s, 2H), δ 2.59 (s, 2H), δ 2.55 (s, 2H), δ 1.63 (m, 6H) ppm; $^{13}$C NMR (75 MHz, CD$_3$OD) δ 175.2, 172.0, 151.2, 134.9, 129.8, 126.0, 116.4, 111.3, 103.8, 44.5, 43.9, 42.9, 42.4, 41.8, 37.9, 23.8 ppm; HRMS (ESI) Calcd for C$_{15}$H$_{16}$N$_4$O$_2$ (M+) 284.1273. Found 284.1278.

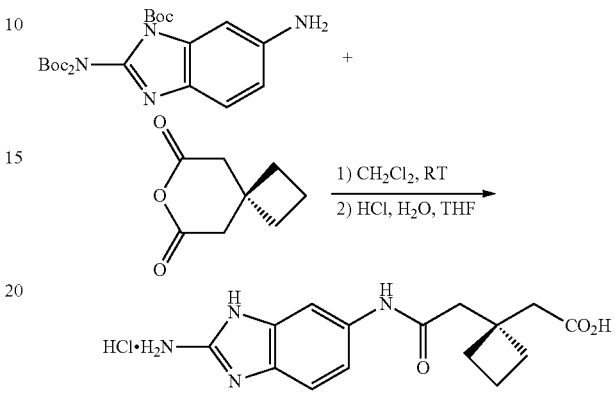

2-(1-(2-(2-amino-1H-benzo[d]imidazol-6-ylamino)-2-oxoethyl)cyclobutyl)acetic acid hydrochloride Following the same procedure to synthesize 2-(2-amino-1H-benzo[d]imidazol-6-ylcarbamoyl)benzoic acid hydrochloride, tert-butyl 6-amino-2-(bis(tert-butoxycarbonyl)amino)-1H-benzo[d]imidazole-1-carboxylate (0.167 g, 0.372 mmol) was reacted with (S)-7-oxaspiro[3.5]nonane-6,8-dione (0.057 g, 0.372 mmol) to give the title product (0.107 g, 85% yield) as a yellow solid. $^1$H NMR (300 MHz, CD$_3$OD) δ 7.49 (s, 1H), δ 6.95 (s, 2H), δ 2.24 (m, 4H), δ 1.32 (m, 8H) ppm; $^{13}$C NMR (75 MHz, CD$_3$OD) δ 175.2, 173.8, 171.8, 151.9, 135.0, 129.7, 116.7, 111.3, 103.9, 44.4, 43.9, 42.0, 39.7, 37.8, 24.1 ppm; HRMS (ESI) Calcd for C$_{15}$H$_{18}$N$_4$O$_3$ (M+) 302.1379. Found 302.1373.

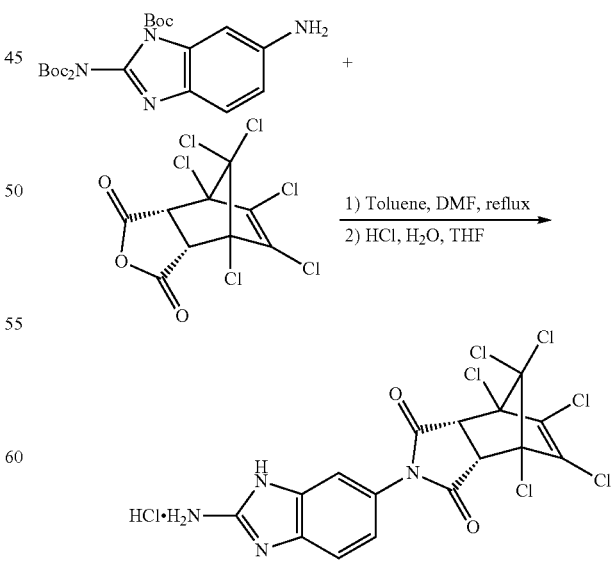

To a 100 mL round-bottomed flask equipped with a magnetic stir bar was added tert-butyl 6-amino-2-(bis(tert-butoxycarbonyl)amino)-1H-benzo[d]imidazole-1-carboxylate (0.100 g, 0.223 mmol), toluene (10 mL), DMF (10 mL) and 1,4,5,6,7,7-hexachloro-5-norbornene-3,3-dicarboxylic anhydride (0.083 g, 0.223 mmol). The stirring solution was allowed to warm to 120° C. and then to continue stirring for two hours. Volatiles were evaporated under reduced pressure. The resulting residue was dissolved up in a 1:1:2 mixture of concentrated HCl, H$_2$O and THF (10 mL) and allowed to stir for seven hours with ventilation. Volatiles were then evaporated under reduced pressure. The resulting solid was rinsed thoroughly with ether providing the product (0.099 g, 83% yield) as a yellow solid. $^1$H NMR (300 MHz, CD$_3$OD) δ 7.50 (d, 1H), δ 7.21 (s, 1H), δ 7.09 (d, 1H), δ 4.23 (s, 2H) ppm; $^{13}$C NMR (75 MHz, CD$_3$OD) δ 170.2, 151.9, 131.3, 130.3, 130.2, 126.9, 122.6, 111.9, 104.2, 79.5 ppm; HRMS (ESI) Calcd for C$_{16}$H$_8$Cl$_6$N$_4$O$_2$(M+) 497.8778. Found 497.8788.

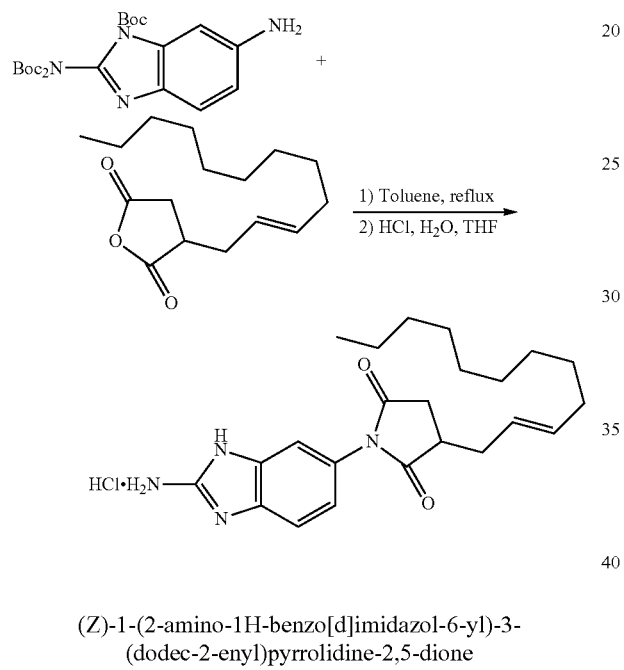

(Z)-1-(2-amino-1H-benzo[d]imidazol-6-yl)-3-(dodec-2-enyl)pyrrolidine-2,5-dione

Following the same procedure to synthesize 1-(2-amino-1H-benzo[d]imidazol-6-yl)-1H-pyrrole-2,5-dione hydrochloride, tert-butyl 6-amino-2-(bis(tert-butoxycarbonyl)amino)-1H-benzo[d]imidazole-1-carboxylate (0.161 g, 0.359 mmol) was reacted with (2-dodecen-1-yl)succinic anhydride (0.096 g, 0.359 mmol) to give the title product (0.142 g, 91% yield) as a yellow solid. $^1$H NMR (300 MHz, CD$_3$OD) δ 7.46 (d, 1H), 7.28 (s, 1H), 7.19 (d, 1H), δ 5.62 (m, 1H), δ 5.47 (m, 1H), δ 3.19 (t, 1H), δ 2.99 (t, 1H), δ 2.65 (m, 2H), δ 2.06 (m, 2H), δ 1.63 (d, 2H), δ 1.28 (m, 14H), δ 0.89 (t, 3H) ppm; $^{13}$C NMR (75 MHz, CD$_3$OD) δ 179.8, 176.9, 151.5, 134.9, 133.7, 129.4, 128.3, 124.9, 122.8, 111.4, 110.6, 40.2, 36.1, 34.9, 33.7, 32.5, 31.9, 29.6, 29.4, 29.1, 27.2, 22.6, 13.4 ppm; HRMS (ESI) Calcd for C$_{23}$H$_{32}$N$_4$O$_2$ (M+) 396.2525. Found 396.2522.

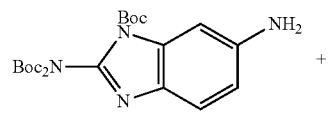

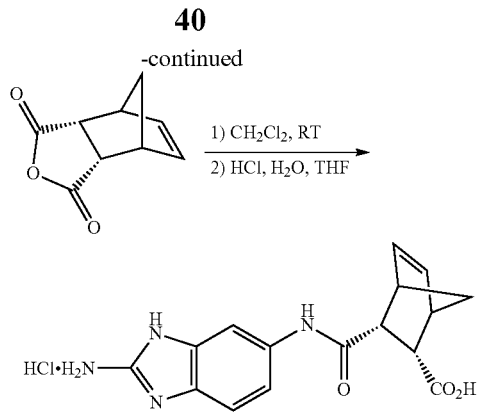

(2S,3R)-3-(2-amino-1H-benzo[d]imidazol-6-ylcarbamoyl)bicyclo[2.2.1]hept-5-ene-2-carboxylic acid hydrochloride (5)

Following the same procedure to synthesize 2-(2-amino-1H-benzo[d]imidazol-6-ylcarbamoyl)benzoic acid hydrochloride (8), tert-butyl 6-amino-2-(bis(tert-butoxycarbonyl)amino)-1H-benzo[d]imidazole-1-carboxylate (0.114 g, 0.254 mmol) was reacted with Bicyclo[2.2.1]hept-5-ene-2,3-dicarboxylic anhydride (0.042 g, 0.254 mmol) to make the title product (0.084 g, 94% yield) as a white solid. $^1$H NMR (300 MHz, CD$_3$OD) δ 7.35 (d, 1H), δ 7.13 (s, 1H), δ 6.99 (d, 1H), δ 6.23 (s, 2H), δ 3.51 (s, 2H), δ 3.37 (s, 2H), δ 1.68 (dd, 2H) ppm; $^{13}$C NMR (75 MHz, CD$_3$OD) δ 178.1, 151.7, 134.8, 134.6, 130.6, 129.8, 129.6, 128.1, 122.8, 111.5, 110.7, 52.0, 46.8, 45.9, 45.5, 45.4 ppm; HRMS (ESI) Calcd for C$_{16}$H$_{16}$N$_4$O$_3$ (M+) 312.1222. Found 312.1226.

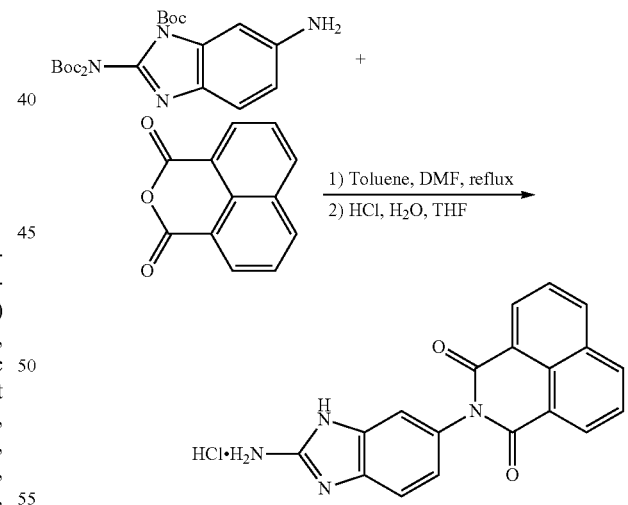

2-(2-amino-1H-benzo[d]imidazol-6-yl)-1H-benzo[de]isoquinoline-1,3(2H)-dione hydrochloride To a 100 mL round-bottomed flask equipped with a magnetic stir bar was added tert-butyl 6-amino-2-(bis(tert-butoxycarbonyl)amino)-1H-benzo[d]imidazole-1-carboxylate (0.096 g, 0.213 mmol), toluene (10 mL), DMF (10 mL) and benzo[de]isochromene-1,3-dione (0.042 g, 0.213 mmol). The stirring solution was allowed to warm to 120° C. and then to continue stirring for two hours. Volatiles were evaporated under reduced pressure. The resulting residue was dissolved up in a 1:1:2 mixture of concentrated HCl, H$_2$O and THF (10 mL) and allowed to stir for seven hours with ventilation. Volatiles were then evaporated under reduced pressure. The resulting solid was rinsed thoroughly with ether providing the title product (0.072 g, 92% yield) as a yellow solid. $^1$H NMR (400 MHz, DMSO) δ 8.76 (s, 1H), δ 8.63 (d, 1H), δ 8.56 (d, 1H), δ 8.41 (d, 1H), δ 8.03 (m, 2H), δ 7.49 (s, 1H), δ 7.43 (d, 1H), δ 7.23 (d, 1H) ppm; $^{13}$C NMR (100 MHz, DMSO) δ 160.9, 160.7, 151.9, 139.2, 133.9, 133.2, 131.8, 131.3, 129.7, 129.6, 129.3, 128.7, 128.1, 120.6, 119.2, 118.6, 112.7, 107.3 ppm; HRMS (ESI) Calcd for C$_{19}$H$_{12}$N$_4$O$_2$ (M+) 328.0960. Found 328.0911.

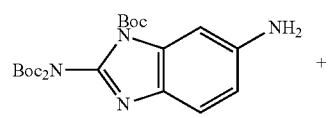

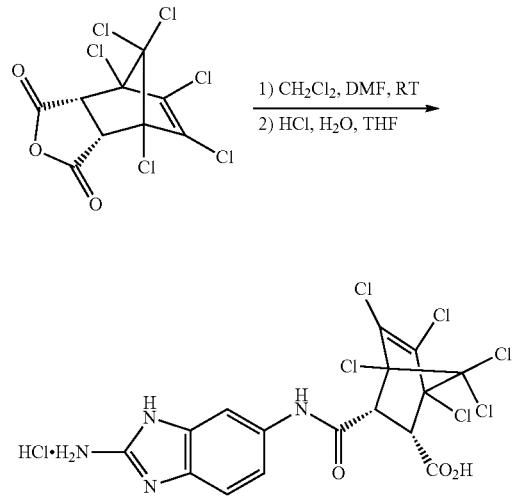

(2S,3R)-3-(2-amino-1H-benzo[d]imidazol-6-ylcarbamoyl)-1,4,5,6,7,7-hexachlorobicyclo[2.2.1]hept-5-ene-2-carboxylic acid hydrochloride To a 100 mL round-bottomed flask equipped with a magnetic stir bar was added tert-butyl 6-amino-2-(bis(tert-butoxycarbonyl)amino)-1H-benzo[d]imidazole-1-carboxylate (0.140 g, 0.313 mmol), dichoromethane (10 mL), DMF (10 mL) and 1,4,5,6,7,7-hexachloro-5-norbornene-3,3-dicarboxylic anhydride anhydride (0.116 g, 0.313 mmol). The stirring solution was allowed stir for 24 hours at room temperature. Volatiles were evaporated under reduced pressure. The resulting residue was dissolved up in a 1:1:2 mixture of concentrated HCl, H$_2$O and THF (10 mL) and allowed to stir for seven hours with ventilation. Volatiles were then evaporated under reduced pressure. The resulting solid was rinsed thoroughly with ether providing the title compound (0.137 g, 79% yield) as a yellow solid. $^1$H NMR (300 MHz, CD$_3$OD) δ 7.54 (s, 1H), δ 7.23 (d, 1H), δ 7.22 (d, 1H) δ 4.25 (s, 2H) ppm; $^{13}$C NMR (75 MHz, CD$_3$OD) δ 170.1, 141.9, 131.3, 130.7, 130.3, 130.2, 127.0, 126.9, 107.5, 104.1, 79.5, 52.6 ppm; HRMS (ESI) Calcd for C$_{16}$H$_{10}$Cl$_6$N$_4$O3 (M+) 515.8884. Found 515.8875.

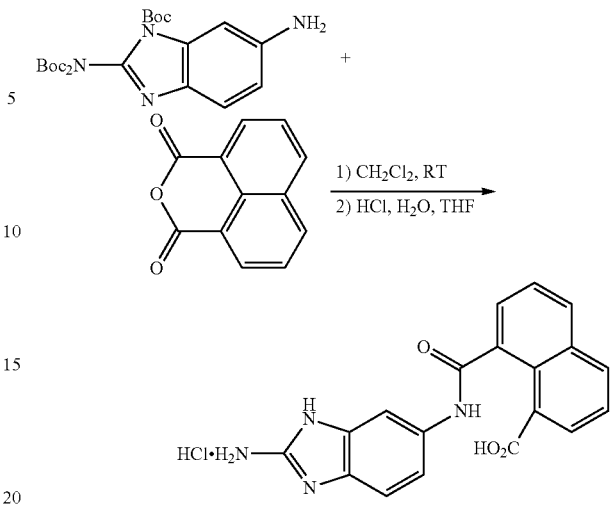

8-(2-amino-1H-benzo[d]imidazol-6-ylcarbamoyl)-1-naphthoic acid hydrochloride (9)

Following the same procedure to synthesize (2S,3R)-3-(2-amino-1H-benzo[d]imidazol-6-ylcarbamoyl)-1,4,5,6,7,7-hexachlorobicyclo[2.2.1]hept-5-ene-2-carboxylic acid hydrochloride (10), tert-butyl 6-amino-2-(bis(tert-butoxycarbonyl)amino)-1H-benzo[d]imidazole-1-carboxylate (0.082 g, 183 mmol) was reacted with benzo[de]isochromene-1,3-dione (0.036 g, 0.183 mmol) to give the title compound (0.067 g, 96% yield) as a white solid. $^1$H NMR (400 MHz, DMSO) δ 11.43-11.21 (bs, 1H), δ 8.75 (s, 2H), δ 8.56 (q, 2H), δ 7.92 (t, 1H), δ 7.47 (s, 2H), δ 7.42 (d, 2H), δ 7.21 (d, 1H) ppm; $^{13}$C NMR (100 MHz, DMSO) δ 161.4, 151.9, 136.1, 133.2, 132.1, 130.9, 130.5, 129.4, 129.8, 129.3, 119.7, 119.3, 112.8, 106.9, 94.6 ppm; HRMS (ESI) Calcd for C$_{19}$H$_{14}$N$_4$O$_3$ (M+) 346.1066. Found 346.1061.

Procedure to Determine the Inhibitory Effect of Test Compounds on E. faecium, MRSA, S. epidermidis, PAO1 and MDRAB Biofilm Formation:

Inhibition assays were performed by taking an overnight culture of bacterial strain and subculturing it at an OD$_{600}$ of 0.01 into the necessary media (brain heart infusion for E. faecium, tryptic soy broth with a 0.5% glucose supplement (TSBG) for MRSA, Luria-Bertani (LB) media for MDRAB, Luria-Bertani media without NaCl (LBNS) for PAO1 and tryptic soy broth with a 0.5% glucose supplement and a 3.0% NaCl supplement (TGN) for S. epidermidis. Stock solutions of predetermined concentrations of the test compound were then made in the necessary media. These stock solutions were aliquoted (100 μL) into the wells of the 96-well PVC microtiter plate. Sample plates were then wrapped in GLAD Press n' Seal® followed by an incubation under stationary conditions for 24 h at 37° C. After incubation, the media was discarded from the wells and the plates were washed thoroughly with water. Plates were then stained with 100 μL of 0.1% solution of crystal violet (CV) and then incubated at ambient temperature for 30 min. Plates were washed with water again and the remaining stain was solubilized with 200 μL of 95% ethanol. A sample of 125 μL of solubilized CV stain from each well was transferred to the corresponding wells of a polystyrene microtiter dish. Biofilm inhibition was quantitated by measuring the OD$_{540}$ of each well in which a negative control lane wherein no biofilm was formed served as a background and was subtracted out. The test compounds demonstrated no biofilm formation inhibitory activity against MDRAB and PAO1 at a 100 µM concentration.

Procedure to Determine the Dispersal Effect of Test Compounds on E. faecium, MRSA and S. epidermidis Preformed Biofilms:

Dispersion assays were performed by taking an overnight culture of bacterial strain and subculturing it at an $OD_{600}$ of 0.01 into the necessary media (brain heart infusion for E. faecium, tryptic soy broth with a 0.5% glucose supplement (TSBG) for MRSA and tryptic soy broth with a 0.5% glucose supplement and a 3.0% NaCl supplement (TGN) for S. epidermidis. The resulting bacterial suspension was aliquoted (100 µL) into the wells of a 96-well PVC microtiter plate. Plates were then wrapped in GLAD Press n' Seal® followed by an incubation under stationary conditions at ambient temperature to establish the biofilms. After 24 h, the media was discarded from the wells and the plates were washed thoroughly with water. Stock solutions of predetermined concentrations of the test compound were then made in the necessary media. These stock solutions were aliquoted (100 µL) into the wells of the 96-well PVC microtiter plate with the established biofilms. Media alone was added to a subset of the wells to serve as a control. Sample Plates were then incubated for 24 h at 37° C. After incubation, the media was discarded from the wells and the plates were washed thoroughly with water. Plates were then stained with 100 µL of 0.1% solution of crystal violet (CV) and then incubated at ambient temperature for 30 min. Plates were washed with water again and the remaining stain was solubilized with 200 µL of 95% ethanol. A sample of 125 µL of solubilized CV stain from each well was transferred to the corresponding wells of a polystyrene microtiter dish. Biofilm dispersion was quantitated by measuring the $OD_{540}$ of each well in which a negative control lane wherein no biofilm was formed served as a background and was subtracted out.

Procedure to Determine the Effect of Compound 3 on E. faecium, MRSA and S. epidermidis Planktonic Viability via Growth Curve Analysis:

Growth curves were performed by taking an overnight culture of bacterial strain and subculturing it at an $OD_{600}$ of 0.01 into the necessary media (brain heart infusion for E. faecium, tryptic soy broth (TSB) for MRSA and nutrient broth (NB) for S. epidermidis). The resulting bacterial suspension was aliquoted (3.0 mL) into culture tubes. The SPAR-1 was then added at a predetermined concentration to the media of the test samples. Controls were employed in which no SPAR-1 was added to the bacterial suspension. Samples were then placed in an incubator at 37° C. and shaken at 200 rpm. The $OD_{600}$ of the samples was measured at time intervals starting at 2 hours and ending at 24 hours.

Colony Count Procedure to Determine the Effect of Compound 3 on E. faecium, MRSA and S. epidermidis Planktonic Viability:

Colony counts were performed by taking an overnight culture of bacterial strain and subculturing it at an $OD_{600}$ of 0.01 into the necessary media (brain heart infusion for E. faecium, tryptic soy broth (TSB) for MRSA and nutrient broth (NB) for S. epidermidis). The resulting bacterial suspension was then aliquoted (3.0 mL) into culture tubes. A test compound was then added to the media of the test samples at a predetermined concentration to the media of the test samples. Controls were employed in which no test compound was added to the bacterial suspension. Samples were then placed in an incubator at 37° C. and shaken at 200 rpm until the $OD_{600}$ of the control samples reached approximately 1.2. At this point, 100 µL was taken from each culture tube and then diluted serially into LB media. Then, 10 µL, was removed from each serial dilution and plated out on a square gridded Petri dish followed by 16 h of incubation at 37° C. to grow viable colonies, which were quantified through employment of the track-dilution method (Jett et al., Simplified agar plate method for quantifying viable bacteria. *Bio Techniques*. 1997, 23, 648-650).

Procedure to Determine the Mitigating Effects of Iron on E. faecium, MRSA and S. epidermidis Biofilm Formation Inhibition Induced by 2-(2-Amino-1H-Benzo[d]Imidazol-6-Ylcarbamoyl)-3,4,5,6-Tetrachlorobenzoic Acid Hydrochloride:

Inhibition assays were performed by taking an overnight culture of bacterial strain and subculturing it at an $OD_{600}$ of 0.01 into the necessary media (brain heart infusion for E. faecium, tryptic soy broth with a 0.5% glucose supplement (TSBG) for MRSA, Luria-Bertani (LB) media for MDRAB, Luria-Bertani media without NaCl (LBNS) for PAO1 and tryptic soy broth with a 0.5% glucose supplement and a 3.0% NaCl supplement (TGN) for S. epidermidis. Stock solutions of predetermined concentrations of the 2-(2-amino-1H-benzo[d]imidazol-6-ylcarbamoyl)-3,4,5,6-tetrachlorobenzoic acid hydrochloride were then made in the necessary media. Samples were then doped with 10.0 µM $FeSO_4$ with samples with no test compound to examine effects of 10.0 µM $FeSO_4$ on biofilm formation. These stock solutions were aliquoted (100 µL) into the wells of the 96-well PVC microtiter plate. Sample plates were then wrapped in GLAD Press n' Seal® followed by an incubation under stationary conditions for 24 h at 37° C. After incubation, the media was discarded from the wells and the plates were washed thoroughly with water. Plates were then stained with 100 µL of 0.1% solution of crystal violet (CV) and then incubated at ambient temperature for 30 min. Plates were washed with water again and the remaining stain was solubilized with 200 µL of 95% ethanol. A sample of 125 µL of solubilized CV stain from each well was transferred to the corresponding wells of a polystyrene microtiter dish. Biofilm inhibition was quantitated by measuring the $OD_{540}$ of each well in which a negative control lane wherein no biofilm was formed served as a background and was subtracted out. 10.0 µM $FeSO_4$ was found to have no effect on biofilm inhibitory activity. However, the 10.0 nM $FeSO_4$ was found to increase biofilm formation for each strain giving 1.37 times the biofilm mass for E. faecium, 1.28 times the biofilm mass for MRSA and 1.25 times the biofilm mass for S. epidermidis.

Procedure to Determine the Mitigating Effects of Zinc on E. faecium, MRSA and S. epidermidis Biofilm Formation Inhibition Induced by 2-(2-Amino-1H-Benzo[d]Imidazol-6-Ylcarbamoyl)-3,4,5,6-Tetrachlorobenzoic Acid Hydrochloride:

Inhibition assays were performed by taking an overnight culture of bacterial strain and subculturing it at an $OD_{600}$ of 0.01 into the necessary media (brain heart infusion for E. faecium, tryptic soy broth with a 0.5% glucose supplement (TSBG) for MRSA, Luria-Bertani (LB) media for MDRAB, Luria-Bertani media without NaCl (LBNS) for PAO1 and tryptic soy broth with a 0.5% glucose supplement and a 3.0% NaCl supplement (TGN) for S. epidermidis. Stock solutions of 50.0 µM 2-(2-amino-1H-benzo[d]imidazol-6-ylcarbamoyl)-3,4,5,6-tetrachlorobenzoic acid hydrochloride were then made in the necessary media. Samples were then doped with 25.0, 50.0, 75.0, 100.0, 150.0 and 200.0 µM $ZnCl_2$ with controls in which no test compound was added to examine effects of 200.0 µM $ZnCl_2$ on biofilm formation. These stock solutions were aliquoted (100 µL) into the wells of the 96-well PVC microtiter plate. Sample plates were then wrapped in GLAD Press n' Seal® followed by an incubation under stationary conditions for 24 h at 37° C. After incubation, the media was discarded from the wells and the plates were washed thoroughly with water. Plates were then stained with 100 μL of 0.1% solution of crystal violet (CV) and then incubated at ambient temperature for 30 min. Plates were washed with water again and the remaining stain was solubilized with 200 μL of 95% ethanol. A sample of 125 μL of solubilized CV stain from each well was transferred to the corresponding wells of a polystyrene microtiter dish. Biofilm inhibition was quantitated by measuring the $OD_{540}$ of each well in which a negative control lane wherein no biofilm was formed served as a background and was subtracted out. 200.0 μM $ZnCl_2$ was found to have no effect on biofilm formation. However, $ZnCl_2$ was found to mitigate the biofilm inhibition response induced by 2-(2-amino-1H-benzo[d]imidazol-6-ylcarbamoyl)-3,4,5,6-tetrachlorobenzoic acid hydrochloride in a dose response manner.

Procedure to Determine the Divalent Zinc Binding Effects of Test Compounds via $^1$H NMR Spectroscopy:

$^1$H NMR Spectra were obtained of the test compounds in DMSO on a 400 MHz NMR in the absence and in the presence of one equivalent of $ZnCl_2$. 2-(2-amino-1H-benzo[d]imidazol-5-ylcarbamoyl)-3,4,5,6-tetrachlorobenzoic acid hydrochloride was tested at a 228 mM. 2,3,4,5-tetrachloro-6-(phenylcarbamoyl)benzoic acid was tested at 275 mM. 1H-benzo[d]imidazol-2-amine hydrochloride was tested at 649 mM.

The foregoing is illustrative of the present invention, and is not to be construed as limiting thereof. The invention is defined by the following claims, with equivalents of the claims to be included therein.

That which claimed is:

1. A compound of Formula (II)(a)(i):

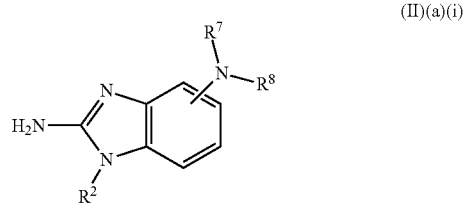

(II)(a)(i)

wherein:
R$^2$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; wherein said R$^2$ may be optionally substituted from 1 to 4 times with independently selected halo, hydroxy, acyl, alkyl, alkenyl, alkynyl, cycloalkyl, heterocyclo, aryl, heteroaryl, alkoxy, amide, thiol, sulfone, sulfoxide, oxo, oxy, carbonyl, or carboxy; and R$^7$ and R$^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein R$^7$ and R$^8$ together form a ring; wherein each of said R$^7$ and R$^8$ may be optionally substituted from 1 to 4 times with independently selected halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, carbonyl, or carboxy;

wherein when R$^7$ or R$^8$ is acyl substituted with phenyl, said phenyl is not substituted with a second phenyl;

or a pharmaceutically acceptable salt thereof.

2. The compound of claim 1, wherein R$^2$ is H or lower alkyl having from 1 to 10 carbon atoms.

3. The compound of claim 1, wherein said compound is a compound of Formula (II)(a)(i)(A):

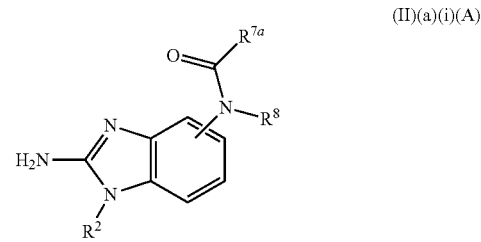

(II)(a)(i)(A)

wherein:
R$^2$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; wherein said R$^2$ may be optionally substituted from 1 to 4 times with independently selected halo, hydroxy, acyl, alkyl, alkenyl, alkynyl, cycloalkyl, heterocyclo, aryl, heteroaryl, alkoxy, amide, thiol, sulfone, sulfoxide, oxo, oxy, carbonyl, or carboxy; and R$^{7a}$ and R$^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein R$^{7a}$ and R$^8$ together form a ring; wherein each of said R$^{7a}$ and R$^8$ may be optionally substituted from 1 to 4 times with independently selected halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, carbonyl, or carboxy;

wherein when R$^{7a}$ is phenyl, said phenyl is not substituted with a second phenyl;

or a pharmaceutically acceptable salt thereof.

4. The compound of claim 3, wherein R$^2$ is H or lower alkyl having from 1 to 5 or from 1 to 10 carbon atoms.

5. The compound of claim 3, wherein R$^{7a}$ is H, alkyl, alkenyl, alkynyl, or aryl.

6. The compound of claim 3, wherein the group at R$^{7a}$ has a carboxy substitution.

7. The compound of claim 3, wherein said compound is:

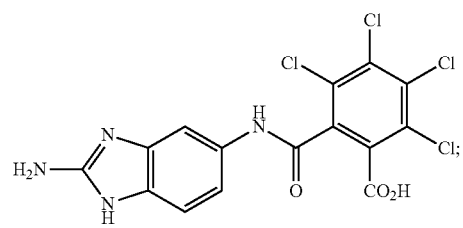 [SMILES: Nc1nc2cc(NC(=O)c3c(Cl)c(Cl)c(Cl)c(Cl)c3C(=O)O)ccc2[nH]1]

or a pharmaceutically acceptable salt thereof.

8. The compound of claim 1, wherein said compound is a compound of Formula (II)(a)(i)(B):

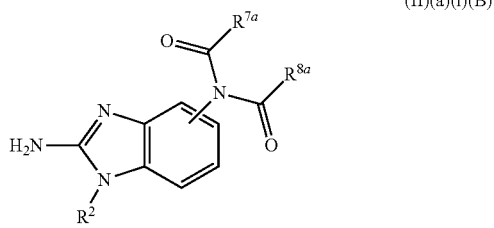

(II)(a)(i)(B)

wherein:
R² is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; wherein said R² may be optionally substituted from 1 to 4 times with independently selected halo, hydroxy, acyl, alkyl, alkenyl, alkynyl, cycloalkyl, heterocyclo, aryl, heteroaryl, alkoxy, amide, thiol, sulfone, sulfoxide, oxo, oxy, carbonyl, or carboxy; and $R^{7a}$ and $R^{8a}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide, or wherein $R^{7a}$ and $R^{8a}$ together form a ring; wherein each of said $R^{7a}$ and $R^{8a}$ may be optionally substituted from 1 to 4 times with independently selected halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, carbonyl, and carboxy;

or a pharmaceutically acceptable salt thereof.

9. The compound of claim 8, wherein R² is H or lower alkyl having from 1 to 5 or from 1 to 10 carbon atoms.

10. The compound of claim 8, wherein said compound is:

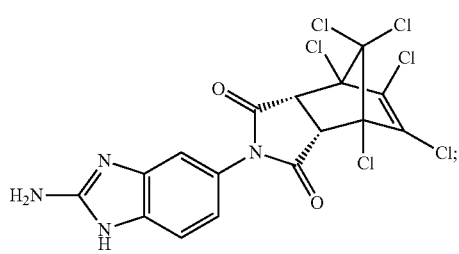 [SMILES: Nc1nc2cc(N3C(=O)[C@@H]4[C@H](C3=O)C3(Cl)C(Cl)=C(Cl)C4(Cl)C3(Cl)Cl)ccc2[nH]1]

or a pharmaceutically acceptable salt thereof.

11. A composition comprising a carrier and an effective amount of the compound of claim 1.

12. The composition of claim 11, wherein said composition is a dentifrice composition that promotes dental hygiene by preventing, reducing, inhibiting or removing a biofilm.

13. The dentifrice composition of claim 12, wherein the dentifrice composition comprises a toothpaste, mouthwash, chewing gum, dental floss, or dental cream or gel.

14. A composition comprising the compound of claim 1 and a biocide.

15. A composition comprising the compound of claim 1 covalently coupled to a substrate.

16. The composition of claim 15, wherein said substrate comprises a polymeric material.

17. The composition of claim 15, wherein said substrate comprises a solid support.

18. The composition of claim 15, wherein said substrate is selected from the group consisting of a drainpipe, glaze ceramic, porcelain, glass, metal, wood, chrome, plastic, vinyl, and laminate.

19. The composition of claim 15, wherein the substrate is selected from the group consisting of shower curtains or liners, upholstery, laundry, and carpeting.

20. The composition of claim 15, wherein said substrate is a ship hull or portion thereof.

21. The composition of claim 15, wherein the substrate is a food contact surface.

22. A biofilm preventing, removing or inhibiting coating composition, comprising:
(a) a film-forming resin;
(b) a solvent that disperses said resin;
(c) an effective amount of the compounds of claim 1, wherein said effective amount of said compound prevents or inhibits the growth of a biofilm thereon; and
(d) optionally, at least one pigment.

23. The coating composition of claim 22, wherein said compound is covalently coupled to said resin.

24. The coating composition of claim 22, wherein said resin comprises a polymeric material.

25. A substrate coated with the coating composition of claim 22.

26. The substrate of claim 25, wherein said substrate comprises a polymeric material.

27. The substrate of claim 25, wherein said substrate comprises a solid support.

28. The substrate of claim 25, wherein said substrate is selected from the group consisting of a drainpipe, glaze ceramic, porcelain, glass, metal, wood, chrome, plastic, vinyl, and laminate.

29. The substrate of claim 25, wherein the substrate is selected from the group consisting of shower curtains or liners, upholstery, laundry, and carpeting.

30. The substrate of claim 25, wherein said substrate is a ship hull or portion thereof.

31. The substrate of claim 25, wherein the substrate is a food contact surface.

32. A method of controlling biofilm formation on a substrate comprising the step of contacting the compound of claim 1 to said substrate in an amount effective to inhibit biofilm formation.

33. A method of controlling biofilm formation on a substrate comprising the step of contacting the composition of claim 11 to the substrate in an amount effective to inhibit biofilm formation.

34. The method of claim 33, wherein said method comprises the step of clearing a preformed biofilm from said substrate by administering an effective amount of the compound of claim 1 to said substrate, wherein said effective amount will reduce the amount of said biofilm on said substrate.

35. The method of claim 34, wherein said method comprises the step of clearing a preformed biofilm from said substrate by administering an effective amount of the composition of claim 11 to said substrate, wherein said effective amount will reduce the amount of said biofilm on said substrate.

36. The method of claim 33, wherein the substrate is selected from the group consisting of a drainpipe, glaze ceramic, porcelain, glass, metal, wood, chrome, plastic, vinyl, and laminate.

37. The method of claim 33, wherein the substrate comprises a food product.

38. The method of claim 37, wherein said food product comprises seafood.

39. The method of claim 33, wherein the biofilm comprises Gram-positive bacteria.

40. The method of claim 33, wherein the biofilm comprises bacteria of the genus selected from the group consisting of: *Listeria, Staphylococcus, Streptococcus, Bacillus, Corynebacterium, Enterococcus, Peptostreptococcus,* and *Clostridium*.

41. The method of claim 33, wherein the biofilm comprises bacteria of the species selected from the group consisting of: *Listeria monocytogenes, Staphylococcus aureus, Staphylococcus epidermidis, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtheriae, Corynebacterium ulcerans, Enterococcus faecium,* and *Peptostreptococcus anaerobius*.

42. A method for treating a chronic bacterial infection in a subject in need thereof, comprising administering to said subject the compound of claim 1 in an amount effective to inhibit, reduce, or remove a biofilm component of said chronic bacterial infection.

43. A method for treating a chronic bacterial infection in a subject in need thereof, comprising administering to said subject the composition of claim 11 in an amount effective to inhibit, reduce, or remove a biofilm component of said chronic bacterial infection.

44. The method of claim 42, wherein said chronic bacterial infection is selected from the group consisting of urinary tract infection, gastritis, respiratory infection, cystitis, pyelonephritis, osteomyelitis, bacteremia, skin infection, rosacea, acne, chronic wound infection, infectious kidney stones, bacterial endocarditis, and sinus infection.

45. A medical device comprising:
   (a) a medical device substrate; and
   (b) an effective amount of the compound of claim 1, either coating the substrate, or incorporated into the substrate, wherein said effective amount of said compound prevents or inhibits the growth of a biofilm thereon.

46. The medical device of claim 45, wherein said medical device substrate is selected from the group consisting of stents, fasteners, ports, catheters, scaffolds and grafts.

47. The medical device of claim 45, wherein said compound is covalently coupled to said substrate.

* * * * *